United States Patent [19]

Ishizumi et al.

[11] Patent Number: 4,745,117
[45] Date of Patent: May 17, 1988

[54] IMIDE DERIVATIVES AND COMPOSITIONS FOR USE AS ANTIPSYCHOTIC AGENTS

[75] Inventors: Kikuo Ishizumi, Toyonaka; Fujio Antoku, Takarazuka; Isamu Maruyama, Kawanishi; Atuyuki Kojima, Takarazuka, all of Japan

[73] Assignee: Sumitomo Pharmaceuticals Company, Limited, Osaka, Japan

[21] Appl. No.: 844,528

[22] Filed: Mar. 27, 1986

[30] Foreign Application Priority Data

| Mar. 27, 1985 | [JP] | Japan | 60-62796 |
| Mar. 27, 1985 | [JP] | Japan | 60-62797 |
| Mar. 27, 1985 | [JP] | Japan | 60-62798 |
| Jun. 25, 1985 | [JP] | Japan | 60-139813 |
| Jul. 23, 1985 | [JP] | Japan | 60-163485 |
| Aug. 13, 1985 | [JP] | Japan | 60-177980 |

[51] Int. Cl.$^4$ .................. A61K 31/495; C07D 417/14
[52] U.S. Cl. .................................... 514/254; 544/361; 544/368
[58] Field of Search ............... 544/361, 368; 514/254

[56] References Cited

U.S. PATENT DOCUMENTS

| 3,398,151 | 8/1968 | Wu | 544/230 |
| 3,717,634 | 2/1973 | Uu et al. | 544/230 |
| 4,182,763 | 1/1980 | Casten et al. | 514/252 |
| 4,411,901 | 10/1983 | Temple et al. | 514/254 |
| 4,479,954 | 10/1984 | Hirose et al. | 544/368 |
| 4,524,206 | 6/1985 | New et al. | 544/368 |
| 4,590,196 | 5/1986 | Smith et al. | 544/368 |

FOREIGN PATENT DOCUMENTS

2114119  8/1983  United Kingdom ............... 544/368

*Primary Examiner*—Donald G. Daus
*Assistant Examiner*—Cecilia Shen
*Attorney, Agent, or Firm*—Birch, Stewart, Kolasch & Birch

[57] ABSTRACT

A compound of the formula:

wherein
A is a carbonyl group or a sulfonyl group;
B is either one of the formulas:

(in which E is a methylene group, an ethylene group or an oxygen atom and a full line accompanying a broken line (———) indicates a single bond or a double bond), (in which F is a methylene group or an ethylene group and a full line accompanying a broken line (———) is as defined above) and (in which $R^1$, $R^2$, $R^3$, $R^4$, $R^5$ and $R^6$ are each a hydrogen atom or a methyl group) when A represents a carbonyl group, or B is a 1,2-phenylene group when A represents a sulfonyl group;
D is an ethylene group, an ethenylene group or an ethynylene group, of which one or more may be optionally substituted with hydroxyl; and
n is an integer of 0, 1 or 2, or its acid addition salt. These compounds are useful for the treatment or psychosis.

16 Claims, No Drawings

IMIDE DERIVATIVES AND COMPOSITIONS FOR USE AS ANTIPSYCHOTIC AGENTS

The present invention relates to imide derivatives, and their production and use. More particularly, the present invention relates to novel imide derivatives, their production processes and their use as antipsychotic agents.

The imide derivatives of this invention are represented by the formula:

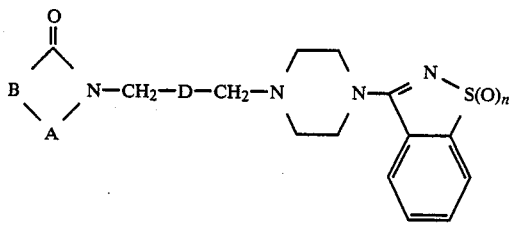

wherein
A is a carbonyl group or a sulfonyl group;
B is either one of the formulas:

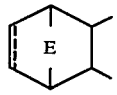

(in which E is a methylene group, an ethylene group or an oxygen atom and a full line accompanying a broken line (=====) indicates a single bond or a double bond),

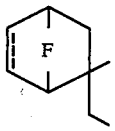

(in which F is a methylene group or an ethylene group and a full line accompanying a broken line (=====) is as defined above) and

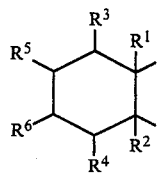

(in which $R^1$, $R^2$, $R^3$, $R^4$, $R^5$ and $R^6$ are each a hydrogen atom or a methyl group) when A represents a carbonyl group, or B is a 1,2-phenylene group when A represents a sulfonyl group;
D is an ethylene group, an ethenylene group or an ethynylene group, which may be optionally substituted with hydroxyl; and
n is an integer of 0, 1 or 2.

As the antipsychotic agents, particularly neuroleptics, there have heretofore been used tricyclic compounds such as chlorpromazine (2-chloro-N,N-dimethyl-10H-phenothiazine-10-propanamine), butyrophenone compounds such as haloperidol (4-[4-(4-chlorophenyl)-4-hydroxy-1-piperidinyl]-1-(4-fluorophenyl)-1-butanone), etc.. However, these conventional neuroleptics produce serious side effects such as catalepsy and hypotension, which cause great problems in their clinical use.

In recent years, some spiroimide compounds have been developed as neuroleptics partly overcoming the drawbacks as seen in conventional neuroleptics. Their typical examples are buspirone (8-[4-(2-pyrimidinyl)-1-piperazinylbutyl]-8-azaspiro[4,5]decane-7,9-dione) and tiaspirone (8-[4-(3-benzisothiazolyl)-1-piperazinylbutyl]-8-azaspiro[4,5]decane-7,9-dione). These spiroimide compounds are alleviated in regard to extrapyramidal side effects such as catalepsy inducing activity in comparison with butyrophenone compounds such as haloperidol. Further, tiaspirone exhibits anti-dopamine activity, as an indication of neuroleptic activity, stronger than chlorpromazine and nearly equal to haloperidol by intraperitoneal administration in anti-climbing behavior tests using apomorphine. Surprisingly, however, the anti-dopamine activity of tiaspirone is drastically reduced by oral administration.

As a result of an intensive studies, it has now been found that the imide derivatives (I) of the present invention exhibit excellent neuroleptic activity with less extrapyramidal side effects. Their anti-dopamine activity as an indication of neuroleptic activity is not lowered even when administered orally. The present invention, therefore, is based on the above finding.

Accordingly, an object of the present invention is to provide the imide derivatives (I) and their pharmaceutically acceptable acid addition salts.

Another object of this invention is to provide processes for production of the imide derivatives (I).

A further object of the present invention is to provide a method of use of the imide derivatives (I) as antipsychotic drugs, particularly neuroleptics.

The imide derivatives (I) can be produced by various processes, of which typical examples are set forth below.

Process (A):

The process comprises the following reaction:

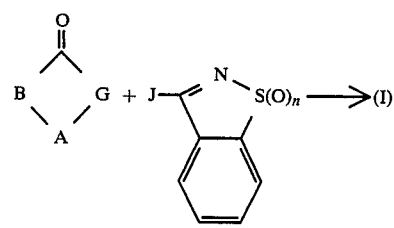

wherein G is —O— and J is

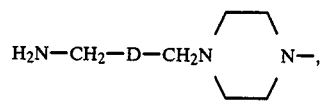

G is —NH— and J is

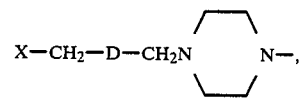

G is —N(CH$_2$—D—CH$_2$—X')— and J is

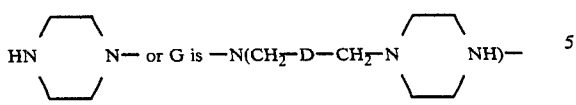 or G is —N(CH$_2$-D—CH$_2$-N NH)— and J is X"—, X, X' and X" are each a leaving group such as halogen (e.g. chlorine, bromine, iodine), alkylsulfonyloxy (e.g. methanesulfonyloxy) or arylsulfonyloxy (e.g. p-toluenesulfonyloxy) and A, B, D and n are each as defined above.

Thus, the above process covers the following four procedures:

Procedure 1

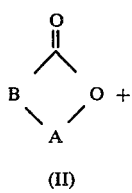 +

(II)

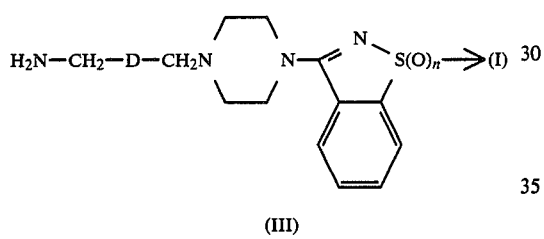

(III)

Procedure 2

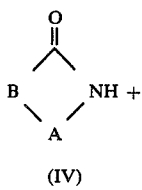 +

(IV)

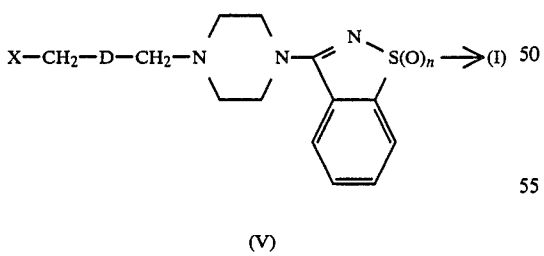

(V)

Procedure 3

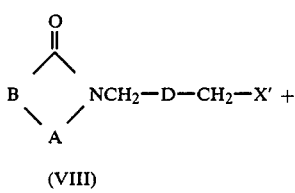 +

(VIII)

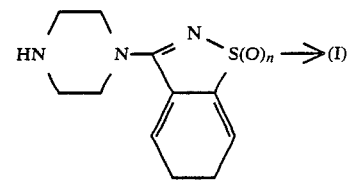

(IX)

Procedure 4

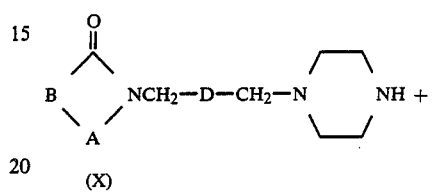 +

(X)

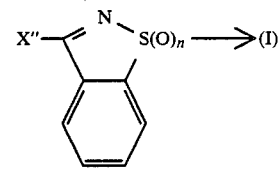

(XI)

wherein A, B, D, G, J, n, X, X40 and X" are each as defined above.

In general, the process (A) is carried out by reacting both of the starting compounds in any inert solvent at such a temperature that the reaction can proceed. The presence of an acid binding agent may be preferred depending upon the kinds of starting materials.

In Procedure 1, the compound (I) is obtained by reacting the compound (II) with the compound (III) in an inert solvent (e.g. pyridine, n-butanol, benzene, toluene, xylene), preferably at reflux temperature.

In Procedure 2, the compound (I) may be prepared by reacting the compound (IV) with the compound (V) in an inert solvent (e.g. benzene, toluene, xylene, dimethylformamide, acetonitrile, n-butanol) in the presence of an acid binding agent, preferably at room temperature or under heating. As the acid-binding agent, there may be used an organic or inorganic base, of which examples are tertiary amines (e.g. triethylamine, pyridine), alkali metal or alkaline earth metal carbonates (e.g. sodium carbonate, potassium carbonate), alkali metal or alkaline earth metal bicarbonates (e.g. sodium bicarbonate, potassium bicarbonate), alkali metal or alkaline earth metal hydrides (e.g. sodium hydride, potassium hydride), etc.

In Procedure 3, the compound (I) is obtained by reacting the compound (VIII) with the compound (IX) in an inert solvent (e.g. benzene, toluene, xylene, dimethylformamide, acetonitrile, n-butanol) in the presence of an acid-binding agent, preferably at room temperature or under heating. As the acid-binding agent, there may be used an organic or inorganic base as exemplified above.

In Procedure 4, the compound (I) is prepared by reacting the compound (X) with the compound (XI) in an inert solvent (e.g. benzene, toluene, xylene, dimethylformamide, acetonitrile, n-butanol) in the presence of an acid-binding agent, preferably at room temperature or under heating. As the acid-binding agent, there may be employed an organic or inorganic base as exemplified above.

The starting compounds (II), (III), (IV), (V), (VIII), (IX), (X) and (XI) in the above Process (A) are known per se or can be produced by any per se conventional procedure. For instance, the compound (II) is described in the following literature and thus known: JP-A-87262/1985; J. Am. Chem. Soc., 63, 3167 (1941); ibid., 72, 1678 (1950), ibid., 74, 3094 (1952), ibid., 73, 4889 (1951).

The compounds (IV), (VIII) and (X) can be produced from the compound (II) by the procedures as described in EP-A-0109562, JP-A-23373/1985, JP-A-87262/1985 and JP-A-87284/1985 according to the following scheme:

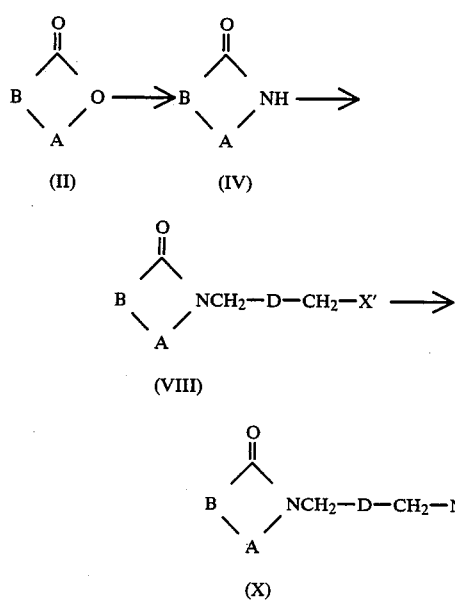

wherein A, B, D, X' and n are each as defined above.

The compounds (III), (V), (IX) and (XI) can be produced according to the following scheme:

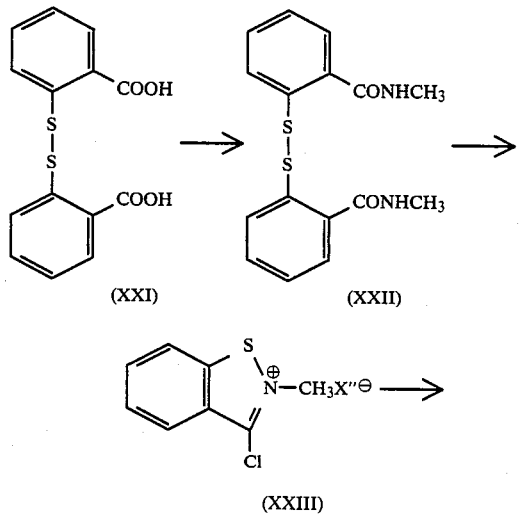

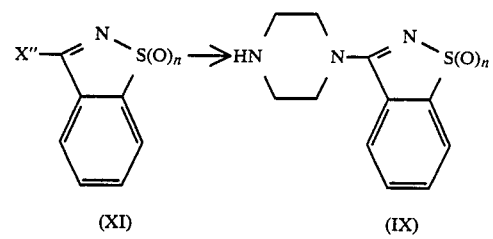

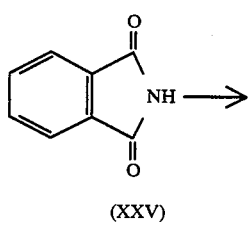

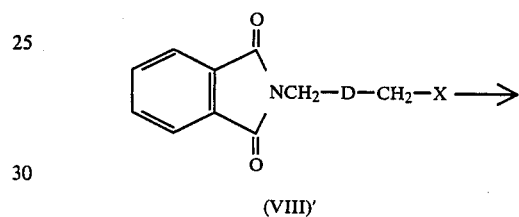

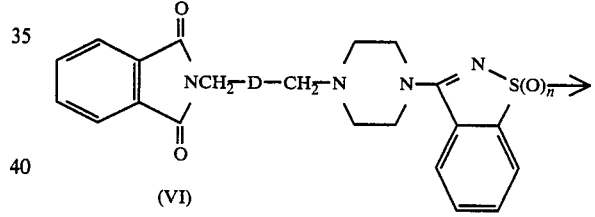

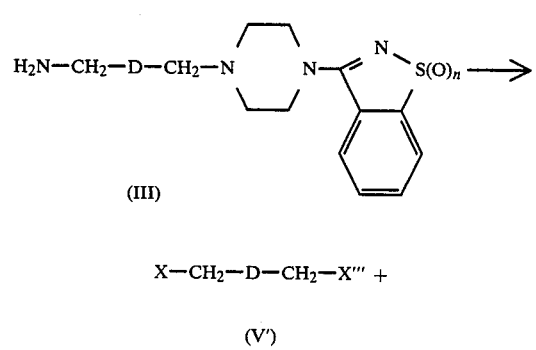

X—CH₂—D—CH₂—X''' +

(V')

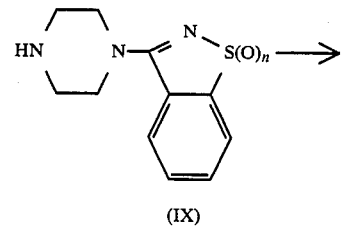

-continued

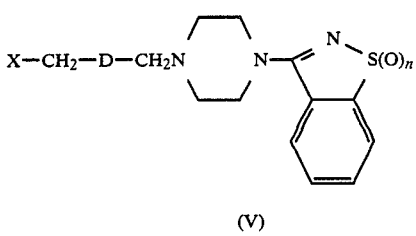

(V)

wherein X''' is a leaving group and D, X, X'' and n are each as defined above.

Namely, the compound (XI) is obtainable from the compound (XXI) through the compounds (XXII) and (XXIII) according to the method as described in Chem. Ber., 99, 2566 (1966). Alternatively, the compound (XI) may be prepared according to the method as described in JP-A-9753/1985. The compound (XI) is then converted into the compound (IX) according to the method as described in JP-A-110576/1983.

The compound (III) may be produced from the compound (XXV) through the compounds (VIII)' and (VI) according to the methods as described in JP-A-87262/1985 and JP-A-216858/1984.

The compound (V) may be obtained by reacting the compound (IX) as above prepared with the compound (V').

Process (B):

The reaction proceeds as shown in the following scheme:

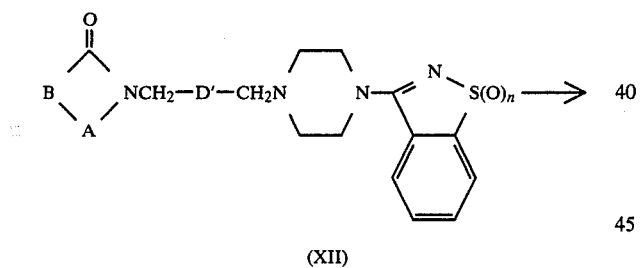

(XII)

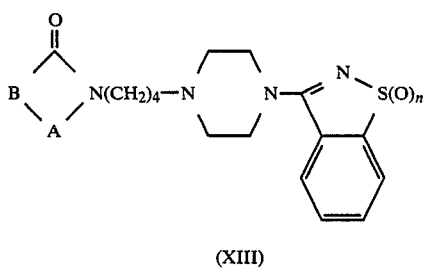

(XIII)

wherein D' is an ethenylene group or an ethynylene group and A, B and n are each as defined above.

Namely, the compound (XIII) is obtainable by hydrogenation of the compound (XII). Hydrogenation may be carried out by any conventional procedure. For instance, catalytic hydrogenation in the presence of a catalyst can be effectively adopted. As the catalyst, there may be used any conventional one such as a metal catalyst (e.g. platinum, palladium, rhodium nickel, cobalt) optionally supported on a carrier (i.e. carbon). Preferably, the reaction is effected in an inert solvent such as benzene, toluene, xylene, methanol, ethanol, ether, tetrahydrofuran, dioxane or ethyl acetate. The reaction can proceed at an ordinary temperature under a normal pressure and may be accelerated by heating and/or pressurization. When desired, the reaction may be controlled by cooling. The reaction is completed by absorption of a theoretical amount of hydrogen. The reaction mixture thus obtained may be subjected to post-treatment by a per se conventional procedure so as to recover the product therefrom, optionally followed by purification.

The starting compound (XII) is obtainable by either one of Processes (A), (C) and (D).

Process (C):

The reaction proceeds in the following way:

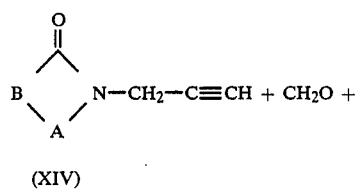

(XIV)

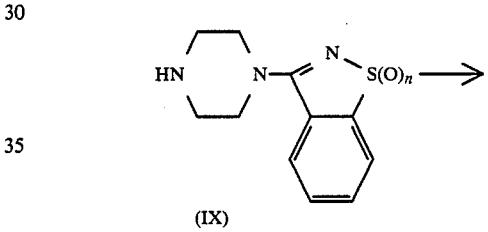

(IX)

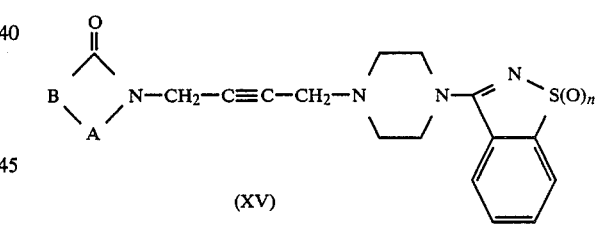

(XV)

wherein A, B and n are each as defined above.

The compound (XV) is obtainable by subjecting the compound (XIV), the compound (IX) and formaldehyde to the Mannich reaction in an inert solvent.

In the reaction, a metallic ion plays a role as the catalyst. Particularly, copper chloride, copper sulfate, copper acetate or iron chloride is useful for this purpose. As the inert solvent, there may be employed water, dioxane, tetrahydrofuran, ether, methylene glycol dimethyl ether, methyl cellosolve, etc. The reaction may be accelerated by heating at a temperature of not higher than the refluxing temperature or controlled by cooling.

The starting compounds (XIV) and (IX) are obtainable by Process (A).

Process (D):

The reaction proceeds as shown in the following scheme:

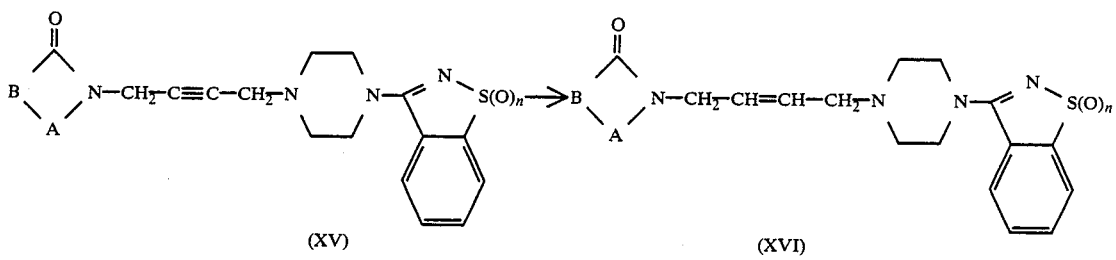

(XV) → (XVI)

wherein A, B and n are each as defined above.

The compound (XVI) is produced by catalytic hydrogenation of the compound (XV). The catalytic hydrogenation may be carried out by treatment of the compound (XV) with hydrogen in the presence of a catalyst, preferably in a liquid medium so as to attain the absorption of an equimolar amount of hydrogen. As the catalyst, there may be employed any one conventionally used for hydrogenation, and its examples are platinum, palladium, rhodium, nickel, cobalt, etc. There may be also employed as the catalyst such a partial reduction catalyst having lesser catalytic activity as palladium-calcium carbonate or palladium-barium sulfate. When desired, the partial reduction catalyst as stated above may be further poisoned with an amine, a sulfur compound or a lead compound so as to reduce its catalytic activity. A typical exmaple is Lyndler catalyst. The catalytic hydrogenation is normally effected in an inert solvent such as benzene, toluene, hexane, methanol, ethanol, diethyl ether, tetrahydrofuran or ethyl acetate.

a controlled condition, e.g. under cooling. After completion of the reaction, the reaction mixture may be subjected to posttreatment by a per se conventional procedure so as to recover the product.

The starting compound (XV) is obtainable by either Process (A) or (C).

Process (E)

The process comprises the following reaction:

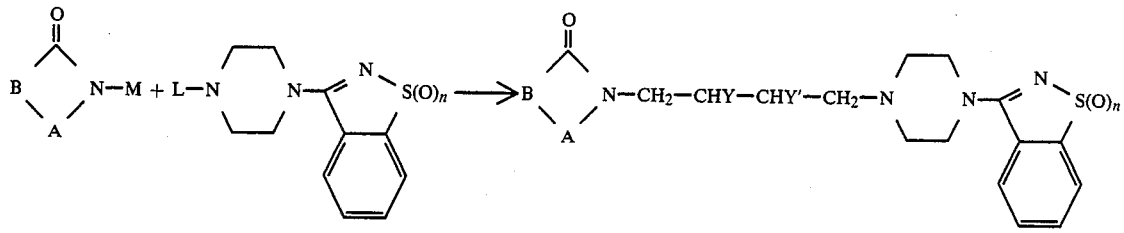

wherein either one of M and L is $$-CH_2CH_2-CHCH_2$$
$$\phantom{-CH_2CH_2-}\backslash/$$
$$\phantom{-CH_2CH_2-}O$$

and the other is a hydrogen atom, either one of Y and Y' is a hydroxyl group and the other is a hydrogen atom, and A, B and n are each as defined above.

Thus, the above process covers the following two procedures:

Procedure 1

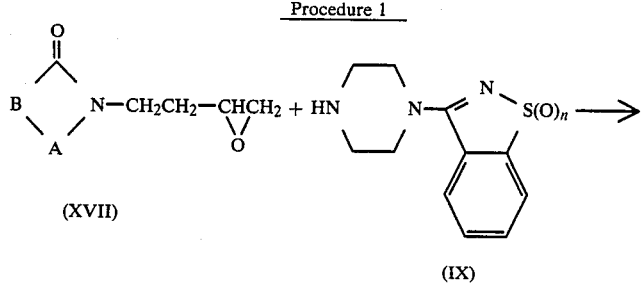

(XVII)                                      (IX)

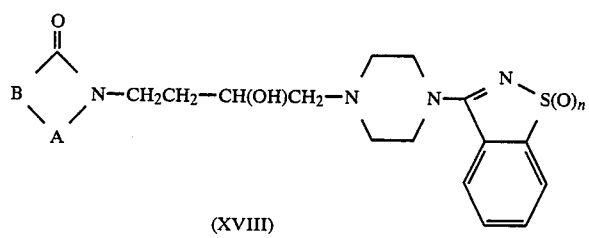

(XVIII)

wherein A, B and n are each as defined above.

The compound (XVIII) is obtained by reacting the compound (XVII) with the compound (IX) in an inert The reaction can proceed at an ordinary temperature under an ordinary pressure, but it may be effected at an elevated temperature and/or under an elevated pressure. If necessary, the reaction may be performed under solvent, preferably at a refluxing temperature. Examples of the inert solvent are benzene, toluene, xylene, dimethylformamide, acetonitrile, n-butanol, etc.

The starting compounds (XVII) and (IX) may be prepared according to Process (A).

Procedure 2

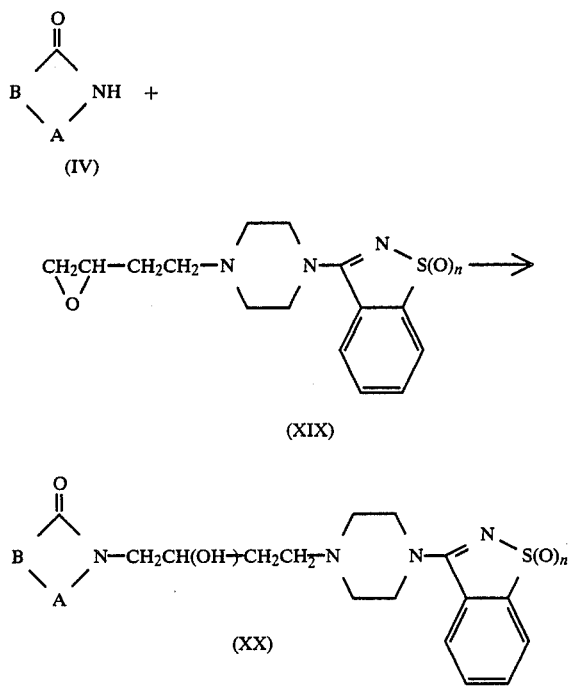

wherein A, B and n are each as defined above.

The compound (XX) is obtained by reacting the compound (IV) with the compound (XIX) in an inert solvent in the presence of a base, preferably at room temperature or under heating. Examples of the inert solvent are benzene, toluene, xylene, dimethylformamide, acetonitrile, n-butanol, etc. As the base, there may be exemplified an organic or inorganic base such as a tertiary amine (e.g. triethylamine, pyridine), an alkali metal or alkaline earth metal carbonate (e.g. sodium carbonate, potassium carbonate), an alkali metal or alkaline earth metal bicarbonate (e.g. sodium bicarbonate, potassium bicarbonate) or an alkali metal or alkaline earth metal hydride (e.g. sodium hydride, potassium hydride).

The starting compounds (IV) and (XIX) may be prepared according to Process (A).

Process (F)

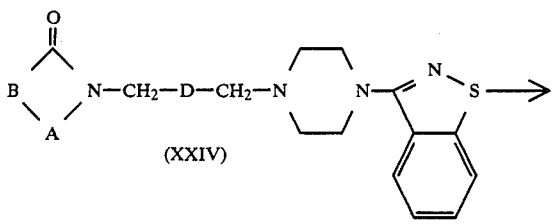

-continued

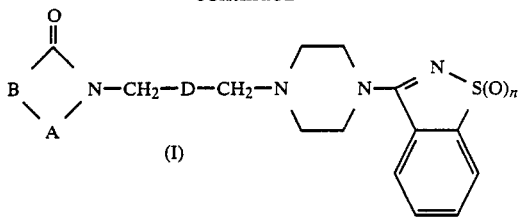

wherein A, B, D and n are each as defined above.

Namely, the compound (I) is obtained by oxidation of the compound (XXIV). The oxidation may be carried out by treatment of the compound (XXIV) with an oxidizing agent in an inert solvent, if necessary, under heating or cooling. Examples of the oxidizing agent are organic peracids (e.g. perbenzoic acid, m-chloroperbenzoic acid, monoperoxyphthalic acid, performic acid, peracetic acid, pertrifluoroacetic acid), hydrogen peroxide, manganese dioxide, chromic acid, periodic acid, N-halogenated carboxylic acid amide, potassium permanganate, etc. The inert solvent may be chosen from hydrocarbons (e.g. pentane, cyclohexane, benzene, toluene), halogenated hydrocarbons (e.g. carbon tetrachloride, chloroform, methylene dichloride, chlorobenzene), alcohols (e.g. methanol, ethanol, butanol), acetic acid, diethyl ether, pyridine, acetone, dimethylformamide, dimethylsulfoxide, etc.

The starting compound (XXIV) can be prepared by Process (A).

The imide derivatives (I) of the present invention can be combined with various kinds of acids to form their acid addition salts. Examples of the acids are hydrochloric acid, hydrobromic acid, hydroiodic acid, sulfuric acid, acetic acid, oxalic acid, citric acid, malic acid, lactic acid, fumaric acid, maleic acid, etc. Treatment of the acid addition salts with alkalis can produce the imide derivatives (I) in a free base form.

As stated above, the imide derivatives (I) of the invention exhibit a significant neuroleptic activity. Yet, they have only a very weak extrapyramidal activity which is a typical side effect as generally observed in conventional neuroleptic drugs of the butyrophenone series and the phenothiazine series. In addition, it may be noted that the neuroleptic activity of conventional spiroimide compounds is remarkably alleviated when administered orally, while that of the imide derivatives (I) according to this invention is kept significant even when administered orally.

The above facts are well evidenced by the pharmacological test data as set forth below.

Test method (1) Neuroleptic activity

This activity was examined through the anti-climbing behavior test, i.e. the test for suppressing the climbing behavior induced by apomorphine in mice. A designated amount of the test compound was orally administered to several groups of dd strain male mice (body-weight, 22 to 25 g; one group, 5 mice), and each of the animals was charged in an individual column cage of 12 cm in diameter and 14 cm in height having metal poles (each pole, 2 mm in diameter) vertically installed and arranged along the periphery at intervals of 1 cm. After 50 minutes, apomorphine (1.0 mg/kg) was subcutaneously injected, and 10 minutes after the injection, the behavior was observed during 10 minutes. Evaluation was made on the basis of the following criteria [P. Protais et al.: Psychopharmacology, 50, 1-6 (1976)]:

| Score | Evaluation |
|---|---|
| 0 | All the paws were on the floor |
| 1 | Only forepaws seized the pole of the cage |
| 2 | All the paws seized the pole of the case; climbing behavior observed discontinuously |
| 3 | Continuous climbing behavior observed |

Climbing behavior control percentage per each dose was calculated by the following equation, and $ED_{50}$ (50% effective dose) was determined thereon:

$$\text{Control percentage (\%)} = \frac{\text{Total scores in control groups} - \text{Total scores in tested groups}}{\text{Total scores in control groups}} \times 100$$

The results are shown in Table 1.

(2) Extrapyramidal activity

This activity was examined through the catalepsy inducing activity test as described in M. Fujiwara et al.: Folia Formacol., Japon: 85, 259–274 (1985). A designated amount of the test compound was orally administered to dd strain male mice (bodyweight, 22 to 27 g), and 1 and 4 hours after the administration, catalepsy induction was checked according to the Wirth et al method. Thus, each of the animals was forced to hang the forepows onto a metal pole of 2.5 mm in diameter horizontally situated at a height of 5 cm to maintain a strained state. The test was made with three replications, and the presence of at least one case where the animal was kept in the strained state over a period of 30 seconds was deemed to have caused catalepsy.

The results are shown in Table 2.

TABLE 1

| Compound | $ED_{50}$ (mg/kg) Subcutaneous administration | $ED_{50}$ (mg/kg) Oral administration |
|---|---|---|
| Compound No. 1 | 0.15 | 2.0 |
| Compound No. 5 | 0.13 | 2.6 |
| Haloperidol | 0.21 | — |
| Tiaspiron | 0.23 | >10 |

TABLE 2

| Compound | $ED_{50}$ (mg/kg) |
|---|---|
| Compound No. 1 | 68.1 |
| Compound No. 5 | 111.9 |
| Haloperidol | <5 |

From the above test results, it is understood that haloperidol used for comparison exhibits a significant neuroleptic activity (i.e. anti-climbing activity) but simultaneously exerts a considerably high level of extrapyramidal activity (i.e. catalepsy inducing activity). The imide derivatives (I) of the invention and tiaspiron show nearly the same significant level in neuroleptic activity when administered subcutaneously, but the activity of the former is much higher than that of the latter when administered orally. Further, the extrapyamidal side effect of the imide derivatives (I) is much less than that of haloperidol. From these facts, it may be concluded that the imide derivatives (I) are neuroleptic drugs having a high selectivity and a high safety. Thus, the imide derivatives (I) are usable not only to ordinary patients with mental disorders but also to patients of old age who are apt to be affected by various side effects. Further, it may be noted that some of the imide derivatives (I) show not only neuroleptic activity but also other useful pharmacological activities such as analgesic activity, anti-allergic activity and circulatory activity.

For therapeutic administration, the imide derivatives (I) or their salts may be used in the form of conventional pharmaceutical preparations such as tablets, capsules, syrups, suspensions, solutions, emulsions and suppositories. Depending upon their administration route such as oral administration, parenteral administration or rectal administration, an appropriate preparation form may be used. In order to make those preparations, the imide derivatives (I) may be combined, if necessary, with suitable additives such as carriers, diluents, fillers, binders and stabilizers. In case of an injection, pharmaceutically acceptable buffers, solubilizers, isotonizers, etc. may be incorporated therein.

While the dosage of the imide derivatives (I) varies with the symptom, the age and weight of the patient, the dosage form, the administration mode and the like, the imide derivatives (I) may be, in general, administered to adults in an amount of about 0.5 to 1000 mg, preferably of about 3 to 500 mg per day in a single dose or divided doses.

Practical and presently preferred embodiments for production of the compound (I) as well as the intermediary compounds (II), (IV), (VIII), (X), (III), (V), (IX), (XI), (XIV), (XVII) and (XIX) are illustratively shown in the following Examples and Reference Examples.

Production of the compound (II)

Reference Example 1

4,5-Dimethyl-4-cyclohexene-1,2-dicarboxylic anhydride $CH_2=C(CH_3)-C(CH_3)=CH_2$ +

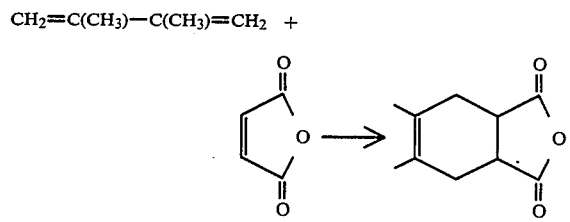

A mixture of 2,3-dimethyl-1,3-butadiene (10 g; 0.122 mol), maleic anhydride (11.9 g; 0.122 mol) and benzene (30 ml) was stirred at room temperature for 10 hours, followed by removal of insoluble materials by filtration. The filtrate was concentrated under reduced pressure to give the objective compound (18.66 g). Yield, 86.6%. M.P., 73°–74° C.

Reference Example 2

4,5-Dimethylcyclohexene-1,2-dicarboxylic anhydride

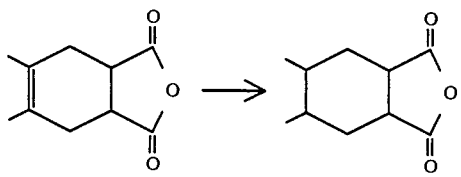

A mixture of 4,5-dimethyl-4-cyclohexene-1,2-dicarboxylic anhydride (10 g; 0.0555 mol), platinum dioxide (150 mg) and tetrahydrofuran (100 ml) was hydrogenated at room temperature for 8 hours, followed by removal of insoluble materials by filtration. The filtrate was concentrated under reduced pressure to give the objective compound quantitatively. IR $\nu_{max}^{film}$ (cm$^{-1}$): 1860, 1760.

In the same manner as in Reference Example 1 or 2, the compounds as shown in Table 3 were obtained.

TABLE 3

| Structure | Physical property |
|---|---|
| (4,5-dimethyl-4-cyclohexene-1,2-dicarboxylic anhydride) | M.P., 43–45° C. |
| (3,6-dimethylcyclohexane anhydride) | IR $\nu_{max}^{film}$ (cm$^{-1}$): 1855, 1790 |
| (1,2-dimethyl-4-cyclohexene dicarboxylic anhydride) | M.P., 98–99° C. |
| (1,2-dimethylcyclohexane dicarboxylic anhydride) | IR $\nu_{max}^{film}$ (cm$^{-1}$): 1845, 1825, 1780 |

Production of the compound (IV)

Reference Example 3

Bicyclo[2.2.2]octane-2,3-dicarboximide

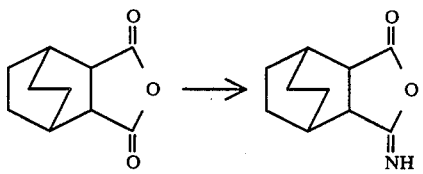

A solution of bicyclo[2.2.2]octane-2,3dicarboxylic anhydride (3 g; 16.6 mmol) in tetrahydrofuran (9 ml) was dropwise added to a mixture of 29% aqueous ammonia (6 g; 83 mmol) in water (18 ml) while ice-cooling, and the resultant mixture was heated. The solvent was removed under atmospheric pressure, and acetic anhydride (10 ml) was added thereto, followed by refluxing for 30 minutes. The solvent was removed under reduced pressure, and the residue was combined with toluene (24 ml) and heated to dissolve. After cooling, the precipitated crystals were collected by filtration to give the objective compound. M.P., 199°–200° C.

Reference Example 4

Cyclohexane-1,2-dicarboximide

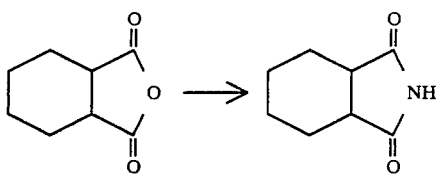

A mixture of cyclohexane-1,2-dicarboxylic anhydride (3 g; 19.5 mmol) and 29% aqueous ammonia (3.4 g) was heated and kept at an inner temperature of 180° to 190° C. for 2 hours to give the objective compound quantitatively. M.P., 132°–136° C.

In the same manner as in Reference Example 3 or 4, the compounds as shown in Table 4 were obtained.

TABLE 4

| Structure | Physical property |
|---|---|
| (norbornane dicarboximide) | M.P., 153–155° C. |
| (norbornane dicarboximide isomer) | M.P., 173–176° C. |
| (methylcyclohexane dicarboximide) | M.P., 75–82° C. |
| (norbornene dicarboximide) | M.P., 187.5–189° C. |
| (norbornene dicarboximide isomer) | M.P., 163.5–164.5° C. |

Production of the compound (VIII):

Reference Example 5

N-(4-Bromobutyl)bicyclo[2.2.1]heptane-2,3-di-exocarboximide:

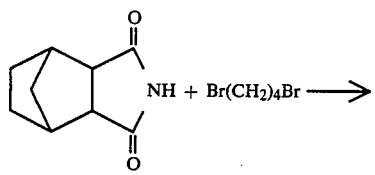

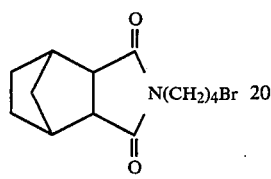

A mixture of bicyclo[2.2.1]heptane-2,3-di-exocarboximide (50 g), anhydrous potassium carbonate (50 g) and acetone (500 ml) was heated under reflux for 5 hours while stirring, followed by cooling. The inorganic substance was removed by filtration and the filtrate was distilled under reduced pressure to give the objective compound as an oily substance (71.4 g). Yield, 78.6%. b.p., 173°–180° C./0.04 mmHg. IR $\nu_{max}^{film}$ (cm$^{-1}$): 1765, 1700, 1430, 1395.

Reference Example 6

N-(4-Bromobutyl)phthalimide:

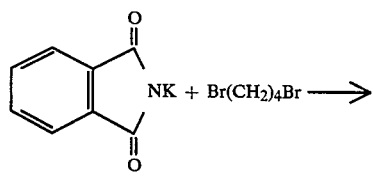

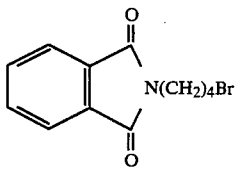

A mixture of phthalimide potassium salt (2 g; 10.8 mmol), 1,4-dibromobutane (10.8 g; 50 mmol) and dry dimethylformamide (10 ml) was stirred at a bath temperature of 90° to 100° C. for 10 hours. The precipitated crystals were removed by filtration, and the filtrate was concentrated under reduced pressure. Excess of 1,4-dibromobutane was removed by distillation, and the residue was purified by silica gel column chromatography to give the objective compound. M.P., 81°–82° C.

Reference Example 7

2-(4-Bromobutyl)-1,2-benzisothiazol-3(2H)-one-1,1-dioxide:

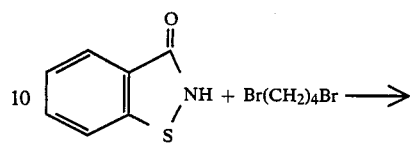

A 60% sodium hydride in mineral oil (1.1 g) was added to dry dimethylformamide (50 ml) at room temperature while stirring. Saccharin (5 g) was gradually added to the suspension at room temperature, followed by stirring for 30 minutes. To the resultant mixture, 1,4-dibromobutane (29.5 g) was dropwise added, and the mixture was kept at an inner temperature of 90° to 100° C. for 5 hours. After completion of the reaction, insoluble materials were removed by filtration, and the filtrate was concentrated under reduced pressure. The residue was purified by silica gel column chromatography using chloroform as an eluent to give the objective compound (7.98 g). IR $\nu_{max}^{film}$ (cm$^{-1}$): 1730, 1595, 1460, 1440, 1330.

In the same manner as in Reference Example 5, 6 or 7, the compounds as shown in Table 5 were obtained.

TABLE 5

$$\underset{A}{\overset{B}{\diagup}} \underset{}{\overset{O}{\diagdown}} N-CH_2-D-CH_2-X \qquad (VIII)$$

| $\underset{A}{\overset{B}{\diagup}} \underset{}{\overset{O}{\diagdown}} N-$ | D | X | Physical property |
|---|---|---|---|
| (norbornane-dicarboximide) | —CH$_2$CH$_2$— | Br | IR $\nu_{max}^{film}$ (cm$^{-1}$): 1765, 1700 |
| (norbornene-dicarboximide) | —CH$_2$CH$_2$— | Br | IR $\nu_{max}^{film}$ (cm$^{-1}$): 1770, 1700 |

TABLE 5-continued $$\underset{A}{\overset{B}{\diagdown}} \underset{}{\overset{O}{\underset{\|}{C}}} N-CH_2-D-CH_2-X \qquad (VIII)$$

| A (with B, N structure) | D | X | Physical property |
|---|---|---|---|
| [norbornene dicarboximide] | —CH₂CH₂— | Br | b.p., 167–170° C./0.15 mmHg |
| [cyclohexane dicarboximide] | —CH₂CH₂— | Br | IR $\nu_{max}^{film}$ (cm$^{-1}$): 1770, 1700 |
| [norbornane dicarboximide] | —CH₂CH₂— | Br | IR $\nu_{max}^{film}$ (cm$^{-1}$): 1760, 1690 |
| [norbornane dicarboximide] | —C(H)=C(H)— | Cl | IR $\nu_{max}^{film}$ (cm$^{-1}$): 1755, 1690 |
| [norbornane dicarboximide] | —CH=CH— | Cl | IR $\nu_{max}^{film}$ (cm$^{-1}$): 1760, 1690 |
| [cyclohexane dicarboximide] | —C(H)=C(H)— | Cl | IR $\nu_{max}^{film}$ (cm$^{-1}$): 1780, 1700 |
| [norbornene dicarboximide] | —C(H)=C(H)— | Cl | IR $\nu_{max}^{film}$ (cm$^{-1}$): 1760, 1700 |
| [methylcyclohexane dicarboximide] | —C(H)=C(H)— | Cl | IR $\nu_{max}^{film}$ (cm$^{-1}$): 1775, 1700 |
| [norbornene dicarboximide] | —C(H)=C(H)— | Cl | IR $\nu_{max}^{film}$ (cm$^{-1}$): 1765, 1705 |
| [norbornane dicarboximide] | —C(H)=C(H)— | Cl | IR $\nu_{max}^{film}$ (cm$^{-1}$): 1760, 1700 |
| [norbornane dicarboximide] | —C(H)=C(H)— | Cl | IR $\nu_{max}^{film}$ (cm$^{-1}$): 1760, 1685–1705 |
| [cyclohexane dicarboximide] | —C≡C— | Cl | IR $\nu_{max}^{film}$ (cm$^{-1}$): 1780, 1700–1720 |

Reference Example 8

N-(4-Bromo-3-hydroxybutyl)cyclohexane-1,2-dicarboximide:

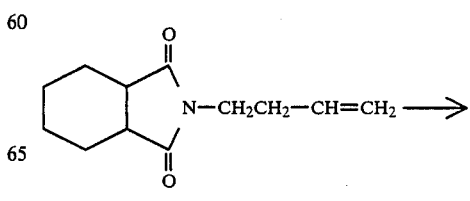

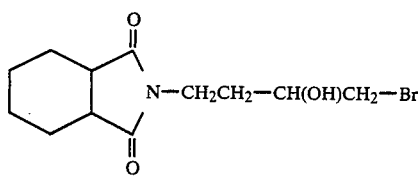

A mixture of N-(3-butenyl)cyclohexane-1,2-dicarboximide (1 g; 4.8 mmol), N-bromosuccinimide (0.86 g; 4.8 mmol) and water (2 ml) was stirred at room temperature for 24 hours. After completion of the reaction, water was added to the reaction mixture to dissolve insoluble materials, followed by extraction with benzene. The benzene layer was washed with a saturated aqueous sodium chloride solution and dried over magnesium sulfate. The solvent was removed under reduced pressure to give the objective compound (1.4 g). Yield, 95.8%. IR $\nu_{max}^{film}$ (cm$^{-1}$): 1760, 1700, 1440, 1400, 1360.

Production of the compound (X):

Reference Example 9

N-(4-Piperazinylbutyl)bicyclo[2.2.1]heptane-2,3-di-exo-carboximide:

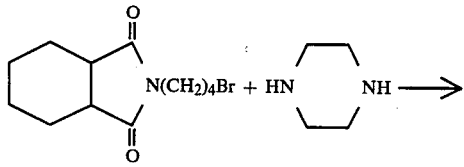

A mixture of N-(4-bromobutyl)bicyclo[2.2.1]heptane-2,3-di-exo-carboximide (30 g; 0.1 mol), piperazine (86 g; 1 mol) and toluene (250 ml) was refluxed for 2 hours, followed by cooling with ice-water. The precipitated crystals were removed by filtration, and the filtrate was concentrated under reduced pressure. The residue was purified by silica gel column chromatography to give the objective compound. IR $\nu_{max}^{film}$ (cm$^{-1}$): 3100–3600 (broad), 1760, 1690.

Production of the compounds (IX) and (XI):

Reference Example 10

3-(1-Piperazinyl)-1,2-benzisothiazole (XXVI):

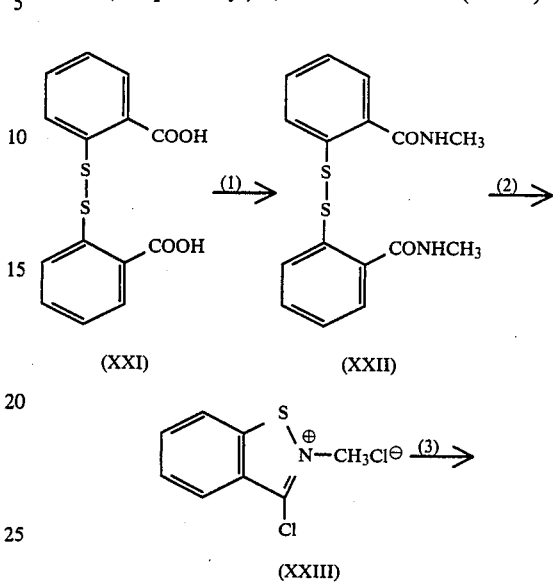

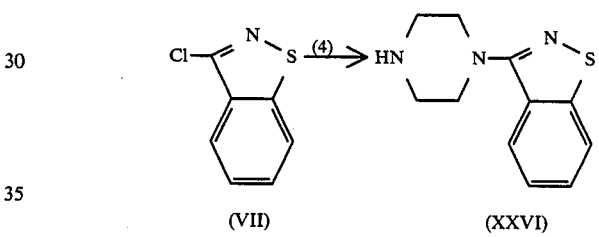

(1) Thionyl chloride (100 ml) was added to 2,2'-dithiobenzoic acid (XXI) (23 g) and heated under reflux for 3.5 hours, whereby crystals were dissolved. The resultant solution was heated under reflux for an additional 30 minutes. After being allowed to cool, excess of thionyl chloride was removed by distillation, whereby the acid chloride (25.8 g) was obtained.

To a mixture of 30% methylamine in ethanol (15.5 g), triethylamine (15.2 g) and ethanol (80 ml), a solution of the acid chloride (25.8 g) in dry tetrahydrofuran (160 ml) was added dropwise, and the resultant mixture was stirred at 25° to 30° C. for 30 minutes. Water (150 ml) was added thereto, followed by stirring for 30 minutes. The precipitated crystals were collected by filtration to give the amide (XXII) (18.9 g). M.P., 217°–219° C.

(2) To a solution of the amide (XXII) (10 g) in dry benzene (60 ml), phosphorus pentachloride (18.8 g) was added, and the mixture was heated under reflux for 2 hours while stirring. After cooling, the precipitated crystals were collected by filtration to give the crude quarternary salt (XXIII) (20 g).

(3) To the crude quarternary salt (XXIII) (20 g) as obtained above, o-dichlorobenzene (40 ml) was added, and the mixture was heated under reflux for 30 minutes. After cooling, insoluble materials were removed by filtration. The filtrate was distilled under reduced pressure to give the benzisothiazole (VII) (5.4 g) as an oily substance. b.p., 125°–133° C./14 mmHg.

(4) Anhydrous piperazine (36.6 g) was added to the chlorobenzisothiazole (4.8 g), and the resultant mixture was stirred at 120° C. for 12 hours. Excess of piperazine was removed by distillation, and dilute sodium hydroxide solution was added to the residue, followed by extraction with dichloromethane. The extract was washed with a saturated aqueous solution of sodium chloride, dried and concentrated under reduced pressure. The residue was purified by chromatography to give the compound (XXVI) (3.5 g). M.P., 87°–91° C.

Reference Example 11

3-Chlorobenzisothiazole-1,1-dioxide:

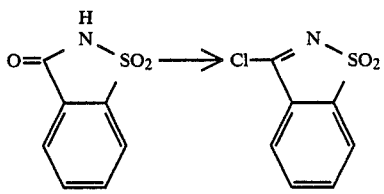

A mixture of saccharin (10 g; 0.055 mol) and phosphorus pentachloride (12.6 g; 0.061 mol) was kept at a bath temperature of 180° C. for 1.5 hours, followed by cooling. To the reaction mixture was added ether (50 ml), followed by vigorous stirring. Crystals were collected by filtration to give the objective compound (3.68 g). Yield, 33%. M.P., 144.5°–145.5° C.

Production of the compound (V):

Reference Example 12

1-(4-Chloro-2-butenyl)-4-(1,2-benzisothiazol-3-yl)piperazine:

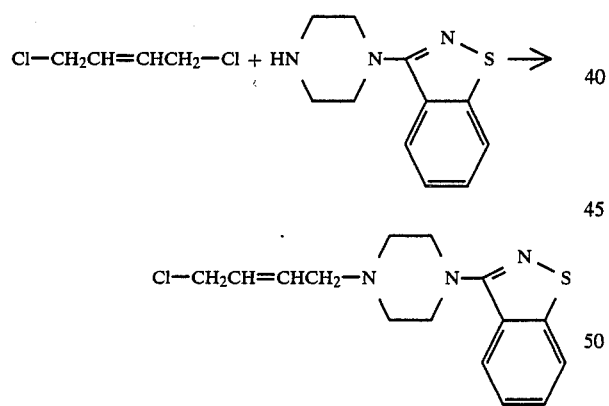

A mixture of 3-(1-piperazinyl)-1,2-benzisothiazole (1 g; 4.56 mmol), 1,4-dichloro-2-butene (2.9 g; 22.8 mmol), anhydrous potassium carbonate (0.79 g; 5.7 mmol) and dry dimethylformamide (10 ml) was stirred at a bath temperature of 90° to 100° C. for 2 hours. After completion of the reaction, toluene (100 ml) was added to the mixture, which was washed three times with water (50 ml). The toluene layer was washed with a saturated sodium chloride solution and dried over magnesium sulfate. The crude oil thus obtained was purified by silica gel chromatography to give the objective compound. IR $\nu_{max}^{Nujol}$ (cm$^{-1}$): 1590, 1560, 1490, 1450, 1420.

Production of the compound (III):

Reference Example 13

1-(4-Aminobutyl)-4-(1,2-benzisothiazol-3-yl)piperazine:

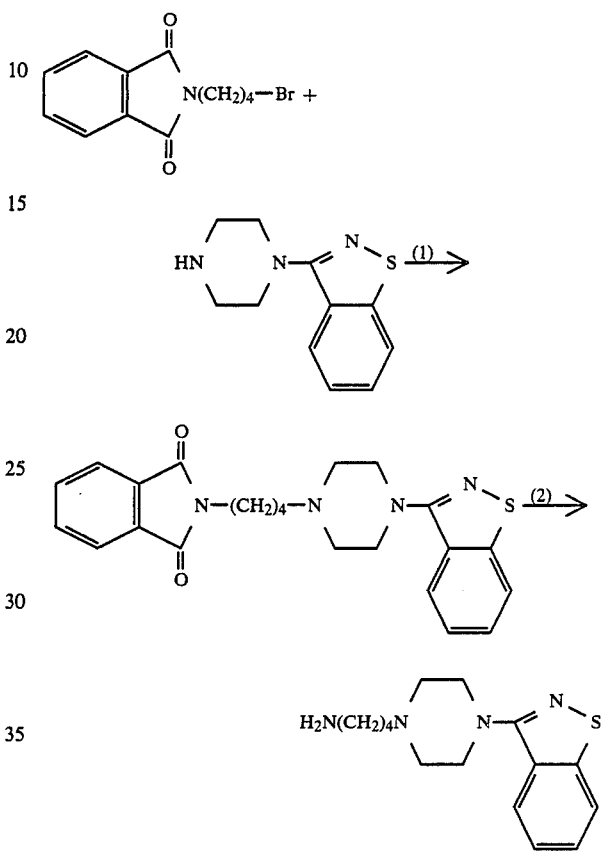

(1) A mixture of 3-(1-piperazinyl)-1,2-benzisothiazole (1 g; 4.6 mmol), potassium carbonate (0.76 g; 5.5 mmol), potassium iodide (0.09 g; 0.55 mmol), N-(4-bromobutyl)phthalimide (1.56 g; 5.5 mmol) and dry dimethylformamide (10 ml) was stirred at a bath temperature of 90° to 100° C. for 3 hours, followed by removal of insoluble materials by filtration. The solvent was removed by distillation under reduced pressure, and the residue was purified by silica gel column chromatography to give the objective compound. M.P., 142°–145° C.

(2) A mixture of N-[4-{4-(1,2-benzisothiazol-3-yl)-1-piperazinyl}butyl]phthalimide (1 g; 2.38 mmol), hydrazine hydrate (0.2 g; 3.57 mmol) and methanol (10 ml) was refluxed for 2.5 hours. After cooling, the reaction mixture was combined with a 10% aqueous hydrochloric acid solution (20 ml) and stirred. The precipitated crystals were removed by filtration, and the filtrate was neutralized with a 10% sodium hydroxide solution and extracted with chloroform. The organic layer was washed with a saturated sodium chloride solution and dried over magnesium sulfate. The solvent was removed under reduced pressure, and the residue was purified by silica gel column chromatography to give the objective compound as an oily substance. IR $\nu_{max}^{film}$ (cm$^{-1}$): 3360, 3280, 3070, 1590, 1560, 1490.

Production of the compound (XIV):

Reference Example 14

N-Propargyl-bicyclo[2.2.1]heptane-2,3-di-exo-carboximide:

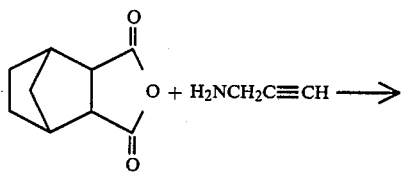

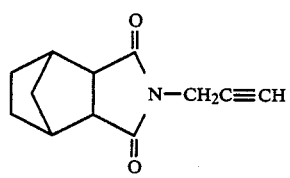

To a solution of propargylamine (1.12 g) in dry tetrahydrofuran (10 ml), a solution of bicyclo[2.2.1]heptane-2,3-di-exo-carboxylic anhydride (1.64 g) in tetrahydrofuran (10 ml) was dropwise added at room temperature under stirring, and the resultant mixture was gradually heated to distill off the solvent and kept at an oily bath temperature of 150° C. for 30 minutes. The residue was purified by chromatography to give the objective compound. Yield, 81%. M.p., 94°-94.5° C.

Reference Example 15

N-Propargyl-bicyclo[2.2.1]heptane-2,3-di-exo-carboximide:

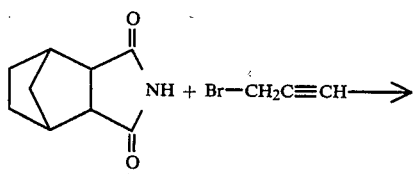

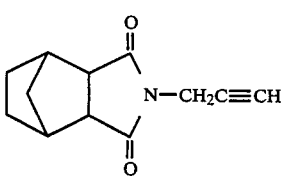

A solution of bicyclo[2.2.1]heptane-2,3-di-exo-carboximide (3.30 g), propargyl bromide (2.62 g) and anhydrous potassium carbonate (3.32 g) in dry acetone (30 ml) was stirred under reflux for 1 hour in nitrogen atmosphere. After cooling, the inorganic materials were removed by filtration, and the filtrate was concentrated under reduced pressure. The residue was combined with chloroform (20 ml) and n-hexane (20 ml) so as to dissolve the crystals. Insoluble materials were removed by filtration with celite, and the filtrate was evaporated. The residue was recrystallized with n-hexane to give the objective compound. Yield, 91%. M.P., 94°-94.5° C.

In the same manner as in Reference Example 14 or 15, the compounds as shown in Table 6 was obtained.

TABLE 6

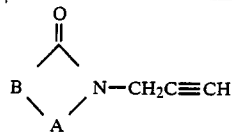

| Structure | Physical property |
|---|---|
| 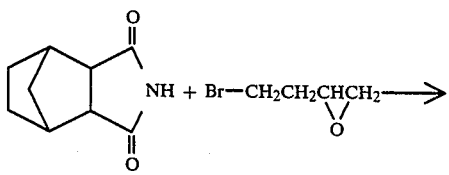 | M.P., 124-126° C. |

Production of the compound (XVII):

Reference Example 16

N-(3,4-Epoxybutyl)bicyclo[2.2.1]heptane-2,3-di-exo-carboximide:

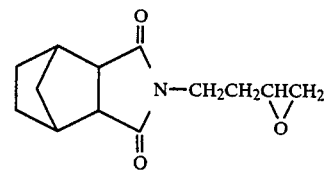

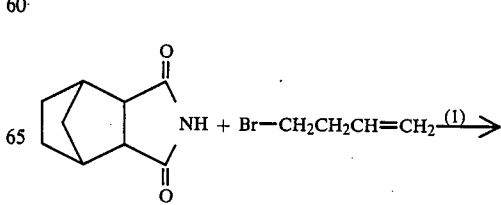

A mixture of bicyclo[2.2.1]heptane-2,3-di-exo-carboximide (2.3 g; 14.2 mmol), 4-bromo-1,2-epoxybutane (2 g; 14.2 mmol), potassium carbonate (2.9 g; 21.3 mmol) and acetone (35 ml) was stirred for 8.5 hours under reflux. After completion of the reaction, the reaction mixture was cooled, and insoluble materials were removed by filtration. The filtrate was concentrated under reduced pressure, the residue was combined with toluene (100 ml), and the resulting mixture was shaken with a saturated aqueous sodium chloride solution (50 ml). The aqueous layer was reextracted with toluene (100 ml), and the toluene layer was combined with the organic layer and dried over magnesium sulfate. The solvent was evaporated under reduced pressure, and the residue was purified by silica gel column chromatography to give the objective compound (2.6 g). Yield, 79.4%. IR $\nu_{max}^{film}$ (cm$^{-1}$): 1765, 1700, 1480, 1440, 1400.

Reference Example 17

N-(3,4-Epoxybutyl)bicyclo[2.2.1]heptane-2,3-di-exo-carboximide:

-continued

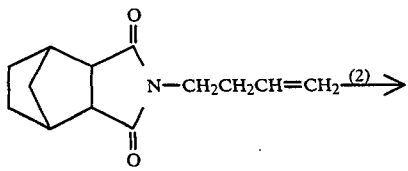

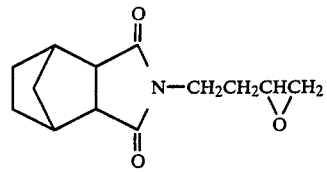

(1) To a mixture of bicyclo[2.2.1]heptane-2,3-di-exo-carboximide (1.65 g) and dimethylformamide (5 ml), a solution of 4-bromo-1-butene (1.62 g) in dimethylformamide (3 ml) was added while stirring at room temperature, followed by addition of anhydrous potassium carbonate (2.07 g). The resultant mixture was heated and allowed to react at an inner temperature of 90° to 100° C. for 1 hour. The reaction mixture was combined with chloroform and subjected to filtration. The filtrate was concentrated under reduced pressure, combined with toluene, washed with water and dried. The solvent was removed under reduced pressure to give the objective compound (2.22 g) as an oily substance. IR $\nu_{max}^{film}$ (cm$^{-1}$): 3050, 3000, 2925, 1485, 1440.

(2) To a solution of N-(3-butenyl)bicyclo[2.2.1]heptane-2,3-di-exo-carboximide (2.65 g) in dichloromethane (15 ml), a solution of m-chloroperbenzoic acid (2.4 g) in dichloromethane (35 ml) was added while stirring at room temperature, and the resultant mixture was allowed to react for 15 hours. After completion of the reaction, the reaction mixture was treated with an aqueous solution of sodium thiosulfate, washed with an aqueous solution of sodium bicarbonate and dried. The solvent was distilled under reduced pressure, and the residue was purified by silica gel column chromatography to give the objective compound (2.03 g) as an oily substance. IR $\nu_{max}^{film}$ (cm$^{-1}$): 1765, 1700, 1480, 1440, 1400.

In the same manner as in Reference Example 16 or 17, the compounds as shown in Table 7 were obtained.

TABLE 7

| ![structure] | Physical property |
|---|---|
| (bicyclo[2.2.1]heptane imide) | IR $\nu_{max}^{film}$ (cm$^{-1}$): 1770, 1700, 1440, 1400 |
| (cyclohexane-fused imide) | IR $\nu_{max}^{film}$ (cm$^{-1}$): 1775, 1710, 1445, 1405, 1355 |
| (methylcyclohexane-fused imide) | IR $\nu_{max}^{film}$ (cm$^{-1}$): 1765, 1700, 1440, 1395, 1350 |
| (norbornene imide) | IR $\nu_{max}^{film}$ (cm$^{-1}$): 1765, 1705, 1440, 1395, 1365 |
| (cyclohexene imide) | IR $\nu_{max}^{film}$ (cm$^{-1}$): 1770, 1700, 1440, 1400, 1365 |
| (tricyclic imide) | IR $\nu_{max}^{film}$ (cm$^{-1}$): 1765, 1680, 1440, 1405, 1390 |

Production of the compound (XIX):

Reference Example 18

3-(3,4-Epoxybutyl-1-piperazinyl)-1,2-benzisothiazole:

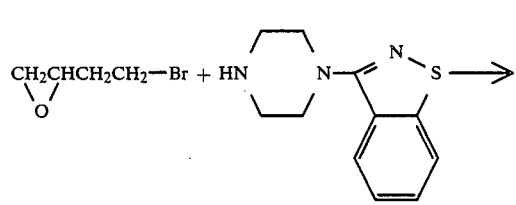

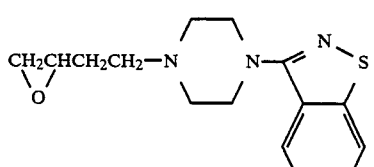

A mixture of 4-bromo-1,2-epoxybutane (1.06 g; 7.02 mmol), 3-(1-piperazinyl)-1,2-benzisothiazole (1.65 g; 7.52 mmol), potassium carbonate (1.6 g; 11.3 mmol) and acetone (20 ml) was stirred under reflux for 19 hours. Confirming complete consumption of the starting materials, insoluble materials were removed by filtration, and the filtrate was concentrated under reduced pressure. The residue was purified by silica gel column chromatography to give the objective compound (1.5 g). Yield, 73.8%. IR $\nu_{max}^{film}$ (cm$^{-1}$): 1590, 1560, 1490, 1460.

Example 1

N-[4-{4-(1,2-Benzisothiazol-3-yl)-1-piperazinyl}butyl]-bicyclo[2.2.1]heptane-2,3-di-exo-carboximide Compound No. 1):

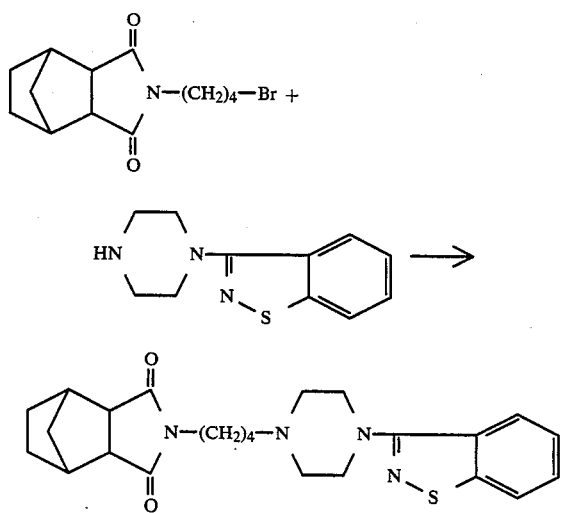

A mixture of N-(4-bromobutyl)bicyclo[2.2.1]heptane-2,3-di-exo-carboximide (1.2 g), 3-(1-piperazinyl)-1,2-benzisothiazole (0.75 g), potassium carbonate (1.2 g), potasium iodide (0.14 g) and acetonitrile (30 ml) was stirred under reflux for 8 hours. Afte completion of the reaction, the reaction mixture was cooled, and insoluble materials were removed by filtration, followed by removal of the solvent by distillation under reduced pressure. The residue was purified by chromatography to give the objective compound. M.P., 217°–218° C.

Example 2

N-[4-{4-(1,2-Benzisothiazol-3-yl)-1-piperazinyl}-2-trans-butenyl]bicyclo[2.2.1]heptane-2,3-di-exo-carboximide (Compound No. 2):

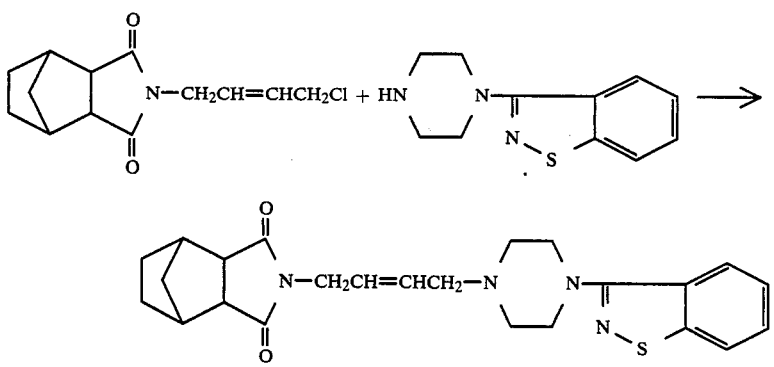

A mixtue of N-(4-chloro-2-trans-butenyl)bicyclo[2.2.1]heptane-2,3-di-exo-carboximide (1.87 g), 3-(1-piperazinyl)-1,2-benzisothiazole (1.5 g), potassium carbonate (1.13 g), potassium iodide (0.11 g) and dimethylformamide (15 ml) was stirred at an inner temperature of 90° to 100° C. for 3 hours. After completion of the reaction, the reaction mixture was cooled and insoluble materials were removed by filtration. The filtrate was evaporated under reduced pressure. The residue was purified by chromatography and treated with hydrogen chloride to give the objective compound. M.P., 214°–215° C.

Example 3

N-[4-{4-(1,2-Benzisothiazol-3-yl)-1-piperazinyl}butyl]-4-methylcyclohexane-1,2-dicarboximide (Compound No. 3):

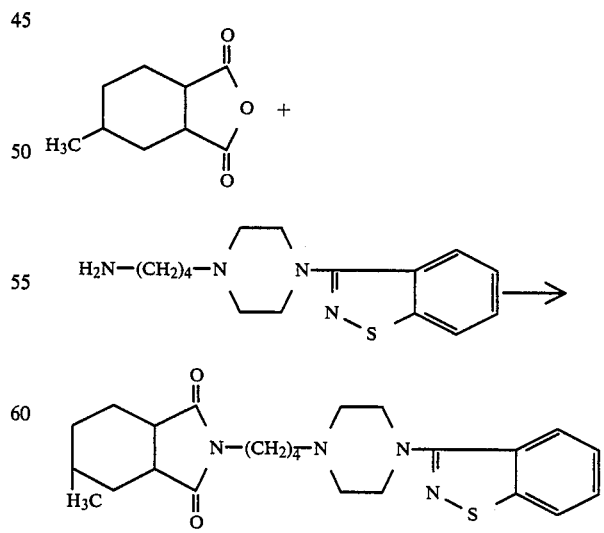

A mixture of 4-methylcyclohexyl-1,2-dicarboxylic anhydride (347 mg; 2.07 mmol), 1-(4-aminobutyl)-4-(1,2-benzisothiazol-3-yl)piperazine (500 mg; 1.72 mmol)

and dry pyridine (5 ml) was refluxed for 11.5 hours. The reaction mixture was distilled under reduced pressure. The residue was purified by silica gel column chromatography and treated with hydrogen chloride to give the objective compound (hydrochloride). M.P., 180°–181° C.

Example 4

N-[4-{4-(1,2-Benzisothiazol-3-yl)-1-piperazinyl}-2-trans-butenyl]bicyclo(2.2.1)heptane-2,3-di-exo-carboximide (Compound No. 2):

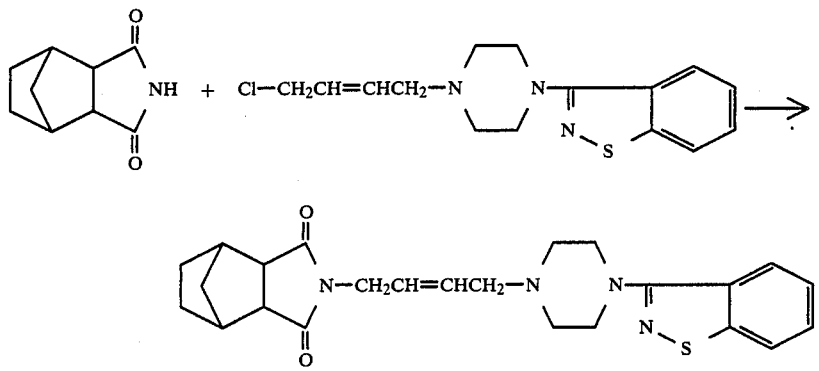

A mixture of 1-(4-chloro-2-butenyl)-4-(1,2-benzisothiazol-3-yl)piperazine (100 mg; 0.32 mmol), anhydrous potassium carbonate (53.9 mg; 0.39 mmol), potassium iodide (6 mg; 0.039 mmol), bicyclo[2.2.1]heptane-2,3-di-exo-carboximide (64 mg; 0.39 mmol) and dry dimethylformamide (1 ml) was stirred at an inner temperature of 90° to 100° C. for 9.5 hours. After completion of the reaction, the reaction mixture was combined with toluene (50 ml) and washed with water (50 ml) three times. The toluene layer was washed with a saturated sodium chloride solution (50 ml) and dried over magnesium sulfate. The solvent was removed under reduced pressure, and the residue was purified by silica gel column chromatography to give the objective compound (43 mg). Yield, 30.8%. IR $\nu_{max}^{film}$ (cm$^{-1}$): 1760, 1660–1700, 1580, 1560. M.P., 214°–215° C. (hydrochloride).

Example 5

N-[4-{4-(1,2-Benzisothiazol-3-yl-1,1-dioxido)-1-piperazinyl}butyl]bicyclo(2.2.1)heptane-2,3-di-exo-carboximide (Compound No. 4):

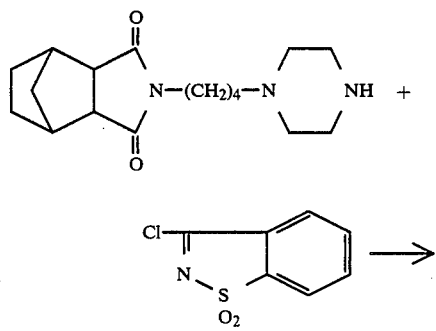

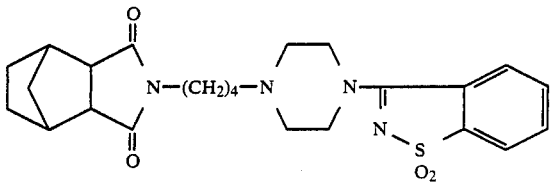

A mixture of N-{4-(1-piperazinyl)butyl}bicyclo[2.2.1]heptane-2,3-di-exo-carboximide (496 mg), 3-chloro-1,2-benzisothiazole-1,1-dioxide (423 mg), potassium carbonate (335 mg) and toluene (20 ml) was stirred at a bath temperature of 110° C. for 1.5 hours. After completion of the reaction, the reaction mixture was cooled, and insoluble materials were removed by filtration. The filtrate was concentrated under reduced pressure. The residue was purified by chromatography to give the objective compound. M.P., 183.5°–185.5° C.

In the same manner as in Examples 1 to 5, the following compounds were obtained:

| Compound No. | Name | M.P. (°C.) |
|---|---|---|
| 5 | N—[4-{4-(1,2-Benzisothiazol-3-yl)-1-piperazinyl}butyl]bicyclo[2.2.1]heptane-2,3-di-endo-carboximide | 213–144 (hydrochloride) |
| 6 | N—[4-{4-(1,2-Benzisothiazol-3-yl)-1-piperazinyl}butyl]bicyclo[2.2.1]hept-5-ene-2,3-di-exo-carboximide | 222–224 (hydrochloride) |
| 7 | N—[4-{4-(1,2-Benzisothiazol-3-yl)-1-piperazinyl}butyl]bicyclo[2.2.1]hept-5-ene-2,3-di-endo-carboximide | 214–216 (hydrochloride) |
| 8 | N—[4-{4-(1,2-Benzisothiazol-3-yl)-1-piperazinyl}butyl]cyclohexane-1,2-dicarboximide | 184–185 (hydrochloride) |
| 9 | N—[4-{4-(1,2-Benzisothiazol-3-yl)-1-piperazinyl}butyl]bicyclo[2.2.2]octane-2,3-dicarboximide | 127–130; 229–231 (hydrochloride) |
| 10 | N—[4-{4-(1,2-Benzisothiazol-3-yl)-1-piperazinyl}butyl]bicyclo[2.2.2]oct-5-ene-2,3-di-endo-carboximide | 141–142 |
| 11 | 2-[4-{4-(1,2-Benzisothiazol-3-yl)-1-piperazinyl}butyl]-1,2-benzisothiazol-3(2H)-one-1,1-dioxide | 224–226 (hydrochloride) |
| 12 | N—[4-{4-(1,2-Benzisothiazol-3-yl)-1-piperazinyl}butyl]-4,5-dimethylcyclohexane-1,2-dicarboximide | 208–210 (hydrochloride) |
| 13 | N—[4-{4-(1,2-Benzisothiazol-3-yl)-1-piperazinyl}butyl]-3,6-dimethylcyclohexane-1,2-dicarboximide | 200–201 (hydrochloride) |
| 14 | N—[4-{4-(1,2-Benzisothiazol-3-yl)-1-piperazinyl}butyl]-1,2-dimethylcyclohexane-1,2-dicarboximide | 245–247 (hydrochloride) |
| 15 | N—[4-{4-(1,2-Benzisothiazol-3-yl)- | 243–244 |

| Compound No. | Name | M.P. (°C.) |
|---|---|---|
| 16 | piperazinyl}butyl]-7-oxabicyclo[2.2.1]heptane-2,3-di-exo-carboximide N—[4-{4-(1,2-Benzimidazol-3-yl)-1-piperazinyl}butyl]bicyclo[2.2.1]-heptane-2-exo-carboxy-2-endo-methylenecarboximide | (hydrochloride) 220–221 (hydrochloride) |
| 17 | N—[4-{4-(1,2-Benzisothiazol-3-yl)-1-piperazinyl}butyl]bicyclo[2.2.1]-hept-5-ene-2-exo-carboxy-2-endo-methylenecarboximide | 196–198 (hydrochloride) |
| 18 | N—[4-{4-(1,2-Benzisothiazol-3-yl)-1-piperazinyl}butyl]bicyclo[2.2.2]-octane-2-exo-carboxy-2-endo-methylenecarboximide | 215–216 (hydrochloride) |
| 19 | N—[4-{4-(1,2-Benzisothiazol-3-yl)-1-piperazinyl}butyl]bicyclo[2.2.2]-oct-5-ene-2-exo-carboxy-2-endo-methylenecarboximide | 194–195 (hydrochloride) |
| 20 | N—[4-{4-(1,2-Benzisothiazol-3-yl)-1-piperazinyl}-2-butynyl]bicyclo[2.2.1]-heptane-2,3-di-exo-carboximide | 98–100 (decomp.) |
| 21 | N—[4-{4-(1,2-Benzisothiazol-3-yl)-1-piperazinyl}-2-trans-butenyl]cyclohexane-1,2-dicarboximide | 209–210 (decomp.; oxalate) |
| 22 | N—[4-{4-(1,2-Benzisothiazol-3-yl)-1-piperazinyl}-2-trans-butenyl]-4-methylcyclohexane-1,2-dicarboximide | 188–190 (decomp.; oxalate) |
| 23 | N—[4-{4-(1,2-Benzisothiazol-3-yl)-1-piperazinyl}-2-trans-butenyl]bicyclo-[2.2.1]hept-5-ene-2,3-di-exo-carboximide | 205–206.5 (decomp.; oxalate) |
| 24 | N—[4-{4-(1,2-Benzisothiazol-3-yl)-1-piperazinyl}-2-trans-butenyl]bicyclo-[2.2.1]heptane-2,3-di-endo-carboximide | 210 (decomp.; oxalate) |
| 25 | N—[4-{4-(1,2-Benzisothiazol-3-yl)-1-piperazinyl}-2-trans-butenyl]bicyclo-[2.2.1]hepti5-ene-2,3-di-endo-carboximide | 210 (decomp.; oxalate) |
| 26 | N—[4-{4-(1,2-Benzisothiazol-3-yl)-1-piperazinyl}-2-trans-butenyl]bicyclo-[2.2.2]octane-2,3-dicarboximide | 200–202 (hydrochloride) |
| 27 | N—[4-{4-(1,2-Benzisothiazol-3-yl)-1-piperazinyl}-2-cis-butenyl]bicyclo-[2.2.1]-heptane-2,3-di-exo-carboximide | 116–118 |
| 28 | N—[4-{4-(1,2-Benzisothiazol-3-yl)-1-piperazinyl}-3-hydroxybutyl]bicyclo-[2.2.1]-heptane-2,3-di-exo-carboximide | 169–170 |
| 33 | N—[4-{4-(1,2-Benzisothiazol-3-yl)-1-piperazinyl}-3-hydroxybutyl]cyclohexane-1,2-dicarboximide | 133–134 |
| 43 | N—[4-{4-(1,2-Benzisothiazol-3-yl)-1-piperazinyl}-2-butynyl]cyclohexane-1,2-dicarboximide | 196–198 (hydrochloride) |

Example 6

N-[4-{4-(1,2-Benzisothiazol-3-yl)-1-piperazinyl}butyl]-bicyclo[2.2.1]heptane-2,3-di-exo-carboximide (Compound No. 1):

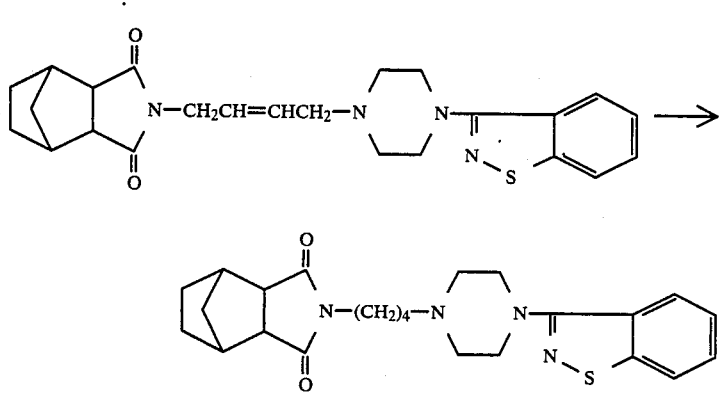

N-[4-{4-(1,2-Benzisothiazol-3-yl)1-piperazinyl}-2-trans-butenyl]bicyclo[2.2.1]heptane-2,3-di-exo-carboximide (0.5 g) was dissolved in tetrahydrofuran (20 ml) containing 10% palladium-carbon (0.5 g) previously treated with hydrogen, and the resulting mixture was stirred at room temperature for 5 hours in a hydrogen stream. After completion of the reaction, the catalyst was removed by filtration, and the filtrate was concentrated under reduced pressure. The residue was treated with hydrogen chloride to give the objective compound. M.P., 217°–218° C. (hydrochloride). In the same manner as in Example 6, the following compounds were obtained.

| Compound No. | Name | M.P. (°C.) |
|---|---|---|
| 3 | N—[4-{4-(1,2-Benzisothiazol-3-yl)-1-piperazinyl}butyl]-4-methylcyclohexane-1,2-dicarboximide | 180–181 (hydrochloride) |
| 5 | N—[4-{4-(1,2-Benzisothiazol-3-yl)-1-piperazinyl}butyl]bicyclo[2.2.1]-heptane-2,3-di-endo-carboximide | 213–214 (hydrochloride) |
| 8 | N—[4-{4-(1,2-Benzisothiazol-3-yl)-1-piperazinyl}butyl]cyclohexane-1,2-dicarboximide | 184–185 (hydrochloride) |
| 9 | N—[4-{4-(1,2-Benzisothiazol-3-yl)-1-piperazinyl}butyl]bicyclo[2.2.2]-octane-2,3-dicarboximide | 229–231 (hydrochloride) |

Example 7

N-[4-{4-(1,2-Benzisothiazol-3-yl)-1-piperazinyl}-2-butynyl]bicyclo[2.2.1]heptane-2,3-di-exo-carboximide (Compound No. 20):

Example 8

N-[4-{4-(1,2-Benzisothiazol-3-yl)-1-piperazinyl}-2-cis-butenyl]bicyclo[2.2.1]heptane-2,3-di-exo-carboximide (Compound No. 27):

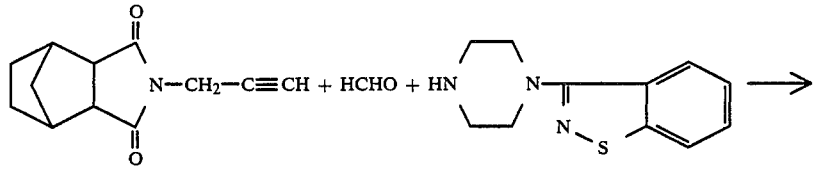

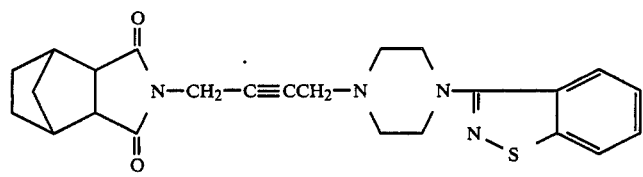

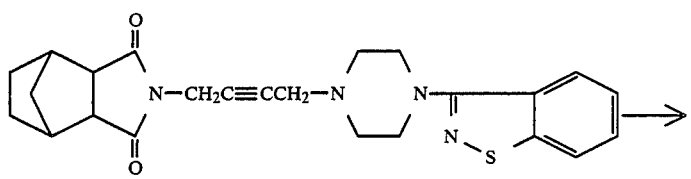

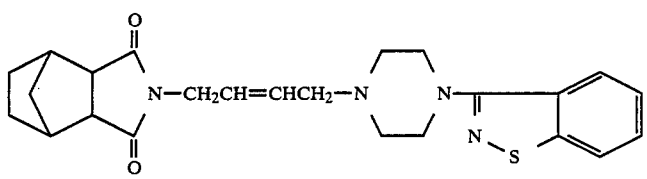

To a solution of N-propargylbicyclo[2.2.1]heptane-2,3-di-exo-carboxmide (406 mg) in dioxane (1 ml), a solution of 1-(1,2-benzisothiazol-3-yl)piperazine (437 mg) in dioxane (1 ml), 35% formalin (0.33 ml) and an aqueous solution of copper sulfate (18 mg) in water (1 ml) were dropwise added while stirring at room temperature, and stirring was continued at 70° to 80° C. for 2 hours. After concentration, the residue was combined with toluene, and insoluble materials were removed by filtration. The filtrate was concentrated under reduced pressure. The residue was purified by chromatography to give the objective compound. M.P., 98°-100° C. (decomp.).

N-[4-{4-(1,2-Benzisothiazol-3-yl)1-piperazinyl}-2-butynyl]bicyclo[2.2.1]heptane-2,3-di-exo-carboximide (0.5 g) was dissolved in tetrahydrofuran (20 ml) containing 5% palladium-barium sulfate (0.5 g) previously treated with hydrogen, and the resulting mixture was stirred at room temperature in hydrogen stream until the equimolar amount of hydrogen was absorbed. After completion of the reaction, the catalyst was removed by filtration. The filtrate was concentrated under reduced pressure. The residue was purified by chromatography to give the objective compound. M.P., 116°-118° C.

Example 9

N-[4-{4-(1,2-Benzisothiazol-3-yl)-1-piperazinyl}-3-hydroxybutyl]bicyclo[2.2.1]heptane-2,3-di-exo-carboximide (Compound No. 28):

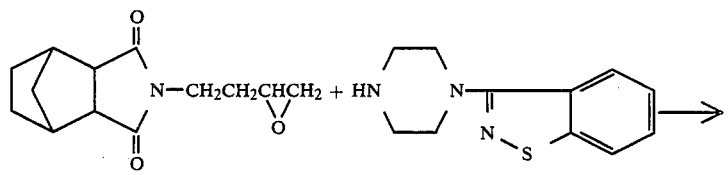

-continued

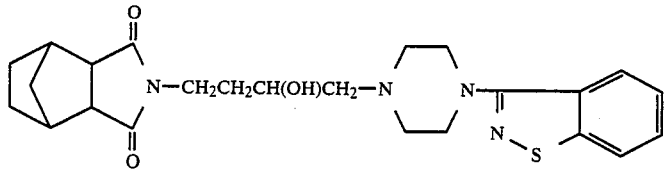

A mixture of N-(3,4-epoxybutyl)bicyclo[2.2.1]heptane-2,3-di-exo-carboximide (1.07 g), 3-(1-piperazinyl)-1,2-benzisothiazole (1.0 g) and n-butanol (20 ml) was stirred under reflux for 12 hours. After completion of the reaction, the solvent was removed under reduced pressure. The precipitated crystals were collected and washed with isopropanol to give the objective compound. M.P., 169°-170° C.

In the same manner as in Example 9, the following compounds were obtained:

| Compound No. | Name | M.P. (°C.) |
|---|---|---|
| 33 | N—[4-{4-(1,2-Benzisothiazol-3-yl)-1-piperazinyl}-3-hydroxybutyl]cyclohexane-1,2-dicarboximide | 133–134 |
| 34 | N—[4-{4-(1,2-Benzisothiazol-3-yl)-1-piperazinyl}-3-hydroxybutyl]-4-methylcyclohexane-1,2-dicarboximide | 174–176 (decomp.; oxalate) |
| 35 | N—[4-{4-(1,2-Benzisothiazol-3-yl)-1-piperazinyl}-3-hydroxybutyl]bicyclo[2.2.1]hept-5-ene-2,3-di-exo-carboximide | 186–187.5 |
| 36 | N—[4-{4-(1,2-Benzisothiazol-3-yl)-1-piperazinyl}-3-hydroxybutyl]bicyclo[2.2.1]heptane-2,3-di-endo-carboximide | 149–151 |
| 37 | N—[4-(4-(1,2-Benzisothiazol-3-yl)-1-piperazinyl-}3-hydroxybutyl]bicyclo[2.2.1]hept-5-ene-2,3-di-endo-carboximide | 153–155 |
| 38 | N—[4-{4-(1,2-Benzisothiazol-3-yl)-1-piperazinyl}-3-hydroxybutyl]bicyclo[2.2.2]octane-2,3-dicarboximide | 155–156 |

Example 10

N-[4-}4-(1,2-Benzisothiazol-3-yl)-1-piperazinyl}-2-hydroxybutyl]bicyclo[2.2.1]heptane-2,3-di-exo-carboximide (Compound No. 39):

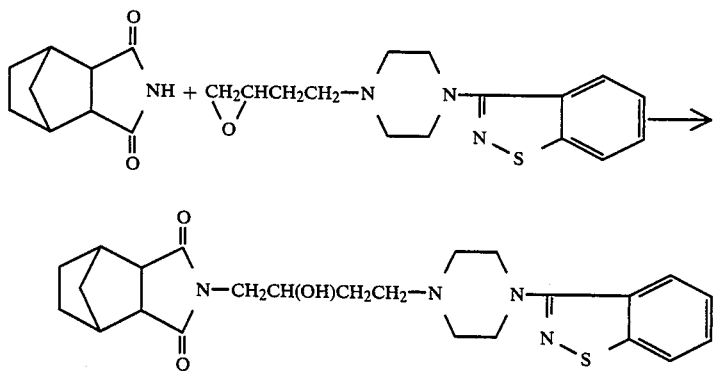

A mixture of 1-(3,4-epoxybutyl)-4-(1,2-benzisothiazol-3-yl)piperazine (0.5 g; 1.73 mmol), bicyclo[2.2.1]heptane-2,3-di-exo-carboximide (0.57 g; 3.46 mmol), potassium carbonate (0.72 g; 5.19 mmol) and n-butanol (13 ml) was stirred under reflux for 9 hours. After completion of the reaction, the reaction mixture was combined with ethyl acetate (100 ml), washed with water (50 ml) two times and dried over magnesium sulfate, followed by removal of the solvent under reduced pressure. The residue was purified by silica gel column chromatography to give the objective compound (375 mg). Yield, 47.7%. M.P., 166°-167° C.

In the same manner as in Example 10, the following compounds were obtained:

| Compound No. | Name | M.P. (°C.) |
|---|---|---|
| 29 | N—[4-{4-(1,2-Benzisothiazol-3-yl)-1-piperazinyl}-2-hydroxybutyl]bicyclo[2.2.1]heptane-2,3-di-endo-carboximide | 195–197 |
| 30 | N—[4-{4-(1,2-Benzisothiazol-3-yl)-1-piperazinyl}-2-hydroxybutyl]bicyclo[2.2.2]octane-2,3-dicarboximide | 145–146.5 |
| 32 | N—[4-{4-(1,2-Benzisothiazol-3-yl)-1-piperzinyl}-2-hydroxybutyl]-4-methylcyclohexane-1,2-dicarboximide | 94–96 (oxalate) |
| 40 | N—[4-{4-(1,2-Benzisothiazol-3-yl)-1-piperazinyl}-2-hydroxybutyl]bicyclo[2.2.1]hept-5-ene-2,3-di-exo-carboximide | 152.5–153.5 |
| 41 | N—[4-{4-(1,2-Benzisothiazol-3-yl)-1-piperazinyl}-2-hydroxybutyl]bicyclo[2.2.1]hept-5-ene-2,3-di-endo-carboximide | 135–136.5 |

Example 11

N-[4-{4-(1,2-Benzisothiazol-3-yl-1,1-dioxide)-1-piperazinyl}butyl]bicyclo[2.2.1]heptane-2,3-di-exo-carboximide (Compound No. 4)

N-[4-{4-(1,2-Benzisothiazol-3-yl-1-oxide)-1-piperazinyl}butyl]bicyclo[2.2.1]heptane-2,3-di-exo-carboximide (Compound No. 42)

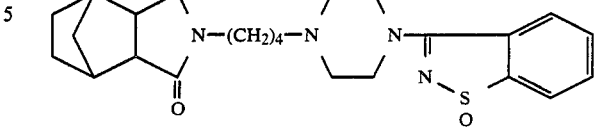

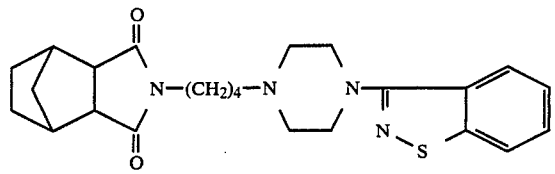

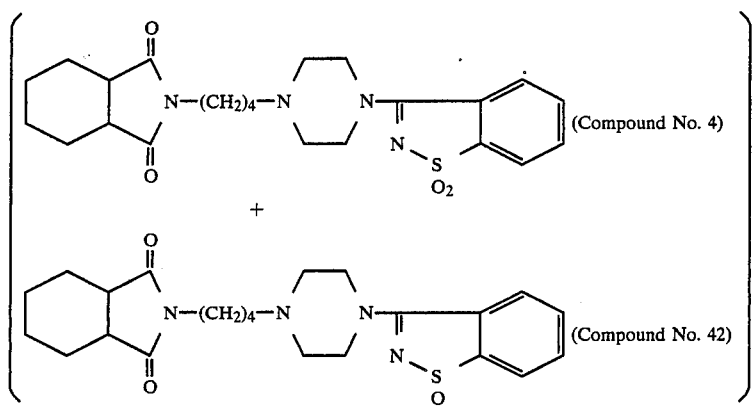

A solution of N-[4-4-(1,2-benzisothiazol-3-yl)-1-piperazinyl butyl]bicyclo[2.2.1]heptane-2,3-di-exo-carboximide hydrochloride (0.5 g; 1.05 mmol) in methylene chloride (40 ml) was dropwise added to m-chloroperbenzoic acid (145 mg; 0.84 mmol) at an inner temperature of −10° C., and the resultant mixture was stirred at the same temperature for 3 hours and further at room temperature for 10 hours. The reaction mixture was combined with a saturated sodium bicarbonate solution (50 ml) and extracted with methylene chloride (100 ml). The organic layer was dried over magnesium sulfate, and the solvent was removed under reduced pressure. The residue was purified by silica gel column chromatography to give the objective compounds. M.P., 150°–155° C. (crude) (Compound No. 4); 188°–191° C. (crude) (Compound No. 42).

Example 12

N-[4-4-(1,2-Benzisothiazol-3-yl-1-oxide)-1-piperazinyl butyl]bicyclo[2.2.1]heptane-2,3-di-exo-carboximide (Compound No. 42)

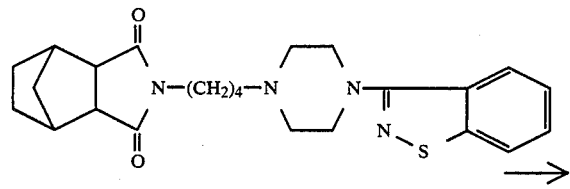

To a solution of N-[4-{4-(1,2-benzisothiazol-3-yl)-1-piperazinyl}butyl]bicyclo[2.2.1]heptane-2,3-di-exocarboximide hydrochloride (0.5 g; 1.05 mmol) in dioxane (5 ml), a solution of sodium bromite (0.3 g) in water (2 ml) was dropwise added, and stirring was continued for 15 minutes. After completion of the reaction, the reaction mixture was extracted with a 2% sodium carbonate solution (50 ml) and ethyl acetate (150 ml) in this order, and the organic layer was washed with a saturated aqueous solution of sodium chloride (50 ml) and dried over magnesium sulfate, followed by removal of the solvent under reduced pressure. The residue was purified by silica gel column chromatography to give the objective compound (200 mg). Yield, 41.8%. M.P., 199°–200° C.

The imide derivatives (I) can be prepared by various procedures as exemplified above. For the sake of reference, Table 8 shows some examples of the imide derivatives (I) and their preparation procedures. In this Table, the numeral under the column "Process" indicates the number of the working example (Example) by which the imide derivative (I) under the column "Compound No." was produced (not parenthesized) or is produced (parenthesized).

TABLE 8

[Structure (I): B-A ring with C=O and N-CH₂-D-CH₂-N(piperazine)-N=C-S(O)ₙ benzisothiazole system]

| Compound No. | B-A ring (with N-) | —D— | n | Physical property | Process |
|---|---|---|---|---|---|
| 1 | bicyclo[2.2.1]heptane-fused imide (norbornane dicarboximide) | —CH₂CH₂— | 0 | 217–218° C. (HCl) | 1, 6 (3, 5) |
| 2 | bicyclo[2.2.1]heptane-fused imide | —CH=CH— (cis) | 0 | 214–215° C. (HCl) | 2, 4 (3, 5) |
| 3 | 4-methylcyclohexane-1,2-dicarboximide | —CH₂CH₂— | 0 | 180–181° C. (HCl) | 3, 6 (1, 5) |
| 4 | bicyclo[2.2.1]heptane-fused imide | —CH₂CH₂— | 2 | 183.5–185.5° C. 150–155° C. (crude) | 5 11 (1, 3, 6) |
| 5 | bicyclo[2.2.2]octane-fused imide | —CH₂CH₂— | 0 | 213–214° C. (HCl) | 1, 6 (3, 5) |
| 6 | bicyclo[2.2.2]oct-2-ene-fused imide | —CH₂CH₂— | 0 | 222–224° C. (HCl) | 1 (3, 5, 6) |
| 7 | bicyclo[2.2.1]hept-2-ene-fused imide | —CH₂CH₂— | 0 | 214–216° C. (HCl) | 1 (3, 5, 6) |

TABLE 8-continued

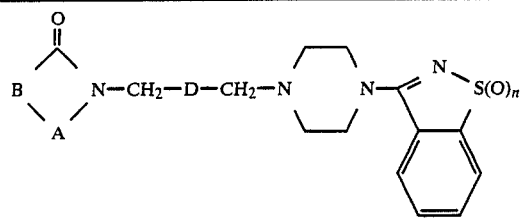
(I)

| Compound No. | ![A/B ring with C=O, N-] | —D— | n | Physical property | Process |
|---|---|---|---|---|---|
| 8 | cyclohexane-fused imide | —CH₂CH₂— | 0 | 184–185° C. (HCl) | 1, 6 (3, 5) |
| 9 | norbornane-fused imide | —CH₂CH₂— | 0 | 229–231° C. (HCl) 127–130° C. | 1, 6 3 (5) |
| 10 | norbornene-fused imide | —CH₂CH₂— | 0 | 141–142° C. | 3 (1, 5, 6) |
| 11 | benzisothiazol-3(2H)-one 1,1-dioxide | —CH₂CH₂— | 0 | 224–226° C. (HCl) | 1 (5, 6) |
| 12 | 4,5-dimethyl cyclohexane-fused imide | —CH₂CH₂— | 0 | 208–210° C. (HCl) | 3 (1, 5, 6) |
| 13 | 3,6-dimethyl cyclohexane-fused imide | —CH₂CH₂— | 0 | 200–201° C. (HCl) | 3 (1, 5, 6) |
| 14 | 3a,7a-dimethyl cyclohexane-fused imide | —CH₂CH₂— | 0 | 245–247° C. (HCl) | 3 (1, 5, 6) |

TABLE 8-continued (I) [Structure: B-A ring with N-CH₂-D-CH₂-N-piperazine-N=C(benzisothiazole-S(O)ₙ)]

| Compound No. | [B-A ring with N—] | —D— | n | Physical property | Process |
|---|---|---|---|---|---|
| 15 | 7-oxa-bicyclic dicarboximide | —CH₂CH₂— | 0 | 243–244° C. (HCl) | 3 (1, 5, 6) |
| 16 | bicyclic spiro succinimide | —CH₂CH₂— | 0 | 220–221° C. (HCl) | 3 (1, 5, 6) |
| 17 | bicyclic ene spiro succinimide | —CH₂CH₂— | 0 | 196–198° C. (HCl) | 3 (1, 5, 6) |
| 18 | bicyclic spiro succinimide | —CH₂CH₂— | 0 | 215–216° C. (HCl) | 3 (1, 5, 6) |
| 19 | bicyclic ene spiro succinimide | —CH₂CH₂— | 0 | 194–195° C. (HCl) | 3 (1, 5, 6) |
| 20 | bicyclic dicarboximide | —C≡C— | 0 | 98–100° C. (dec.) | 2, 7 (4) |

TABLE 8-continued

| Compound No. | A-B (N-) structure | —D— | n | Physical property | Process |
|---|---|---|---|---|---|
| 21 | cyclohexane-fused succinimide | —CH=CH— | 0 | 209–210° C. (dec.; oxalate) | 2 (3, 4, 5) |
| 22 | 5-methylcyclohexane-fused succinimide | —CH=CH— | 0 | 188–190° C. (dec.; oxalate) | 2 (3, 4, 5) |
| 23 | cyclohexene-fused succinimide | —CH=CH— | 0 | 205–206.5° C. (dec.; oxalate) | 2 (3, 4, 5) |
| 24 | norbornane-fused succinimide | —CH=CH— | 0 | 210° C. (dec.; oxalate) | 2 (3, 4, 5) |
| 25 | norbornene-fused succinimide | —CH=CH— | 0 | 210° C. (dec.; oxalate) | 2 (3, 4, 5) |
| 26 | bicyclic-fused succinimide | —CH=CH— | 0 | 200–202° C. (HCl) | 2 (3, 4, 5) |
| 27 | norbornane-fused succinimide | —CH=CH— | 0 | 116–118° C. | 2, 8 (3, 4, 5) |

TABLE 8-continued
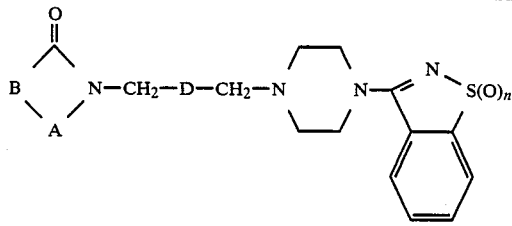
(I)
| Compound No. | A, B (with N—) | —D— | n | Physical property | Process |
|---|---|---|---|---|---|
| 28 | norbornane-dicarboximide | —CH₂CH(OH)— | 0 | 169–170° C. | 2, 9 (3, 4, 5) |
| 29 | norbornane-dicarboximide | —CH(OH)CH₂— | 0 | 195–197° C. | 10 (2, 3, 4, 5) |
| 30 | bicyclic dicarboximide | —CH(OH)CH₂— | 0 | 145–146.5° C. | 10 (2, 3, 4, 5) |
| 31 | hexahydrophthalimide | —CH(OH)CH₂— | 0 | | (2, 3, 4, 5, 10) |
| 32 | methyl-hexahydrophthalimide | —CH(OH)CH₂— | 0 | 94–96° C. (oxalate) | 10 (2, 3, 4, 5) |
| 33 | hexahydrophthalimide | —CH₂CH(OH)— | 0 | 133–134° C. | 2, 9 (3, 4, 5) |
| 34 | methyl-hexahydrophthalimide | —CH₂CH(OH)— | 0 | 174–176° C. (dec.; oxalate) | 9 (2, 3, 4, 5) |

TABLE 8-continued

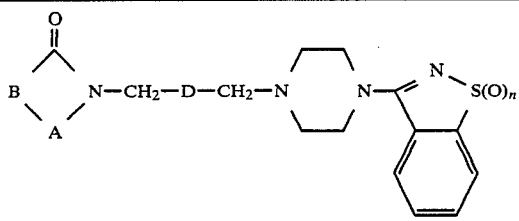

| Compound No. | 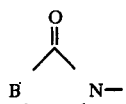 | —D— | n | Physical property | Process |
|---|---|---|---|---|---|
| 35 | (norbornene dicarboximide) | —CH₂CH—<br>  \|<br>  OH | 0 | 186–187.5° C. | 9<br>(2, 3, 4, 5) |
| 36 | (norbornane dicarboximide) | —CH₂CH—<br>  \|<br>  OH | 0 | 149–151° C. | 9<br>(2, 3, 4, 5) |
| 37 | (norbornene dicarboximide) | —CH₂CH—<br>  \|<br>  OH | 0 | 153–155° C. | 9<br>(2, 3, 4, 5) |
| 38 | (bicyclic dicarboximide) | —CH₂CH—<br>  \|<br>  OH | 0 | 155–156° C. | 9<br>(2, 3, 4, 5) |
| 39 | (norbornane dicarboximide) | —CHCH₂—<br>  \|<br>  OH | 0 | 166–167° C. | 10<br>(2, 3, 4, 5) |
| 40 | (norbornene dicarboximide) | —CHCH₂—<br>  \|<br>  OH | 0 | 152.5–153.5° C. | 10<br>(2, 3, 4, 5) |
| 41 | (norbornene dicarboximide) | —CHCH₂—<br>  \|<br>  OH | 0 | 135–136.5° C. | 10<br>(2, 3, 4, 5) |

TABLE 8-continued

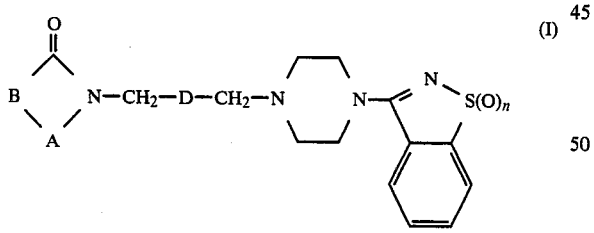

| Compound No. | B‹A›N— | —D— | n | Physical property | Process |
|---|---|---|---|---|---|
| 42 | 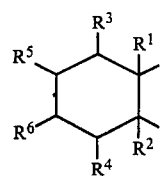 | —CH₂CH₂— | 1 | 199–200° C.<br>188–191° C. (crude) | 12<br>11<br>(1, 3, 5, 6) |
| 43 | 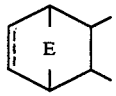 | —C≡C— | 0 | 196–198° C. (HCl) | 2<br>(4, 7) |

The above examples should not be construed to limit the scope of the present invention thereto. In other words, other embodiments of the imide derivatives (I) will be able to be readily produced with reference to the description as set forth herein above and those are to be construed as being within the scope of the present invention.

What is claimed is:

1. A compound of the formula:

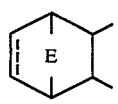 (I)

wherein

A is a carbonyl group or a sulfonyl group;

B is either one of the formulas:

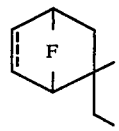

(in which E is a methylene group, an ethylene group or an oxygen atom and a full line accompanying a broken line (=====) indicates a single bond or a double bond), (in which F is a methylene group or an ethylene group and a full line accompanying a broken line (=====) is as defined above) and (in which $R^1$, $R^2$, $R^3$, $R^4$, $R^5$ and $R^6$ are each a hydrogen atom or a methyl group) when A represents a carbonyl group, or B is a 1,2-phenylene group when A represents a sulfonyl group;

D is an ethylene group, an ethenylene group or an ethynylene group, of which one or more may be optionally substituted with hydroxyl; and n is an integer of 0, 1 or 2, or its acid addition salts.

2. The compound according to claim 1, wherein A is a carbonyl group and B is a group of the formula:

(in which E is a methylene group, an ethylene group or an oxygen atom and a full line accompanying a broken line (═════) indicates a single bond or a double bond).

3. The compound according to claim 1, wherein A is a carbonyl group and B is a group of the formula:

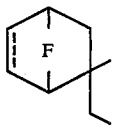

(in which F is a methylene group or an ethylene group and a full line accompanying a broken line (═════) is as defined above).

4. The compound according to claim 1, wherein A is a carbonyl group and B is a group of the formula:

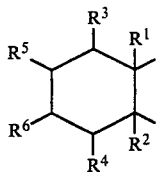

(in which $R^1$, $R^2$, $R^3$, $R^4$, $R^5$ and $R^6$ are each a hydrogen atom or a methyl group).

5. The compound according to claim 1, wherein the group of the formula:

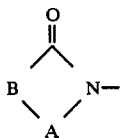

is a group of the formula:

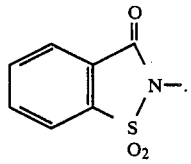

6. A pharmaceutical composition having neuroleptic activity which comprises as an essential active ingredient a neuroleptically effective amount of at least one compound and its pharmaceutically acceptable acid addition salt as claimed in claim 1, and at least one pharmaceutically acceptable inert carrier or diluent.

7. A method for the treatment of a condition requiring neuroleptic activity which comprises administering to a person a pharmaceutically effective amount of at least one compound and its pharmaceutically acceptable acid addition salt as claimed in claim 1.

8. The method of claim 7, wherein said pharmaceutically effective amount is administered in an amount of about 0.5 to 1000 mg per day.

9. The compound according to claim 1, which is N-[4-{4-(1,2-Benzisothiazol-3-yl)-1-piperazinyl}-butyl]-bicyclo[2.2.1]heptane-2,3-di-exo-carboximide.

10. The composition according to claim 6, wherein said at least one compound is N-[4-{4-(1,2-Benzisothiazol-3-yl)-1-piperazinyl}butyl]bicyclo[2.2.1]heptane-2,3-di-exo-carboximide.

11. A pharmaceutical composition having neuroleptic activity which comprises as an essential active ingredient a neuroleptically effective amount of at least one compound and its pharmaceutically acceptable acid addition salt as claimed in claim 2, and at least one pharmaceutically acceptable inert carrier or diluent.

12. A pharmaceutical composition having neuroleptic activity which comprises as an essential active ingredient a neuroleptically effective amount of at least one compound and its pharmaceutically acceptable acid addition salt as claimed in claim 3, and at least one pharmaceutically acceptable inert carrier or diluent.

13. A pharmaceutical composition having neuroleptic activity which comprises as an essential active ingredient a neuroleptically effective amount of at least one compound and its pharmaceutically acceptable acid addition salt as claimed in claim 4, and at least one pharmaceutically acceptable inert carrier or diluent.

14. A pharmaceutical composition having neuroleptic activity which comprises as an essential active ingredient a neuroleptically effective amount of at least one compound and its pharmaceutically acceptable acid addition salt as claimed in claim 5, and at least one pharmaceutically acceptable inert carrier or diluent.

15. The compound according to claim 1, which is N-[4-{4-(1,2-benzisothiazol-3-yl)-1-piperazinyl}-butyl]-cyclohexane-1,2-dicarboximide.

16. The composition according to claim 9, wherein said at least one compound is N-[4-{4-(1,2-benzisothiazol-3-yl)-1-piperazinyl}-butyl]cyclohexane-1,2-dicarboximide.

* * * * *